(12) United States Patent
Buhimschi et al.

(10) Patent No.: US 8,263,342 B2
(45) Date of Patent: Sep. 11, 2012

(54) URINARY PROTEOMIC BIOMARKER PATTERNS IN PREECLAMPSIA

(75) Inventors: Catalin S. Buhimschi, New Haven, CT (US); Irina Buhimschi, New Haven, CT (US)

(73) Assignee: Yale University, New Haven, CT (US)

( * ) Notice: Subject to any disclaimer, the term of this patent is extended or adjusted under 35 U.S.C. 154(b) by 565 days.

(21) Appl. No.: 12/084,004

(22) PCT Filed: Oct. 27, 2006

(86) PCT No.: PCT/US2006/042585
§ 371 (c)(1),
(2), (4) Date: Sep. 25, 2009

(87) PCT Pub. No.: WO2007/051069
PCT Pub. Date: May 3, 2007

(65) Prior Publication Data
US 2010/0035284 A1    Feb. 11, 2010

Related U.S. Application Data

(60) Provisional application No. 60/730,888, filed on Oct. 27, 2005.

(51) Int. Cl.
*G01N 33/53* (2006.01)
(52) U.S. Cl. .......................... 435/7.1; 436/518
(58) Field of Classification Search ........................ None
See application file for complete search history.

(56) References Cited

U.S. PATENT DOCUMENTS

2003/0211471 A1 * 11/2003 Hammond et al. ............... 435/5
2005/0202508 A1 *  9/2005 Pasinetti ......................... 435/7.1

FOREIGN PATENT DOCUMENTS

EP    1016410 A    7/2000
WO   WO 2006/069373 A2    6/2006

OTHER PUBLICATIONS

Stimson et al. (Clin. Biochem. 1972 vol. 5, p. 3-12).*
Legge et al. (J. Clin. Pathol. 1984 vol. 37, p. 867-869).*
PCT/US2006/042585 International Search Report, completed Aug. 27, 2007; mailed Sep. 11, 2007.
[No Author Listed], "Human Alpha-1-Antitrypsin Antibody, Affinity Purified, HRP conjugated," Internet Article (Online); Oct. 29, 2004, URL: http://web.archive.org/web/20041029233853/http://www.bethyl.com/pdf/A80-122P.pdf, retrieved Jul. 9, 2007.
[No Author Listed], "Human Albumin ELISA Quantitation Kit," Internet Article (Online), Oct. 25, 2004, URL: http://web.archive.org/web/20030925234756/http://www.bethyl.com/pdf/E80-129.pdf, retrieved Jul. 9, 2007.
[No Author Listed], "Human P/GF Immunoassay, Catalog No. DEP00," Internet Article (Online) Apr. 2005, URL: http://www.rndsystems.com/pdf/dpg00.pdf, retrieved Jul. 9, 2007.
Bouton, E. et al., "Microalbuminuria and pregnancy. Is microalbuminuria predictive of pregnancy toxemia?," *J. de Gynecol. Obstet. Biol. Reprod.*, 1992, vol. 21, No. 4, pp. 363-369.
Ekbom et al., The Copenhagen Pre-Eclampsia in Diabetic Pregnancy Study, "Pre-pregnancy microalbuminuria predicts pre-eclampsia in insulindependent diabetes mellitus," *Lancet*, 1999, vol. 353, No. 9150, p. 377.
Irgens-Moller, L. et al., "Diagnostic value of microalbuminuria in pre-eclampsia," *Clinica Chimica Acta; Int'l J. of Clin. Chem.*, 1986, vol. 157, No. 3, pp. 295-298.
Shinagawa, S. et al., "A study on proteins contained in urine of gestosis patients," *Biol. Res. in Pregnancy and Perinatology*, 1983, vol. 4, No. 4, pp. 140-144.

* cited by examiner

*Primary Examiner* — Jacob Cheu
(74) *Attorney, Agent, or Firm* — Wolf, Greenfield & Sacks, P.C.

(57) ABSTRACT

The invention relates, in part, to methods of using proteomic biomarkers to diagnose preeclampsia. In some aspects the invention, in part, relates to the detection of serpina-1 polypeptide and/or albumin polypeptide in samples from pregnant subjects. Samples from subjects may be compared to control samples to diagnose preeclampsia and/or to determine the onset, progression, or regression of preeclampsia in a subject. The invention also relates, in part, to screening methods to identify agents that can be used to treat preeclampsia and to determine the efficacy of a preeclampsia treatment. The invention, in part, also includes kits that are useful to diagnose and assess preeclampsia in a subject.

15 Claims, 7 Drawing Sheets

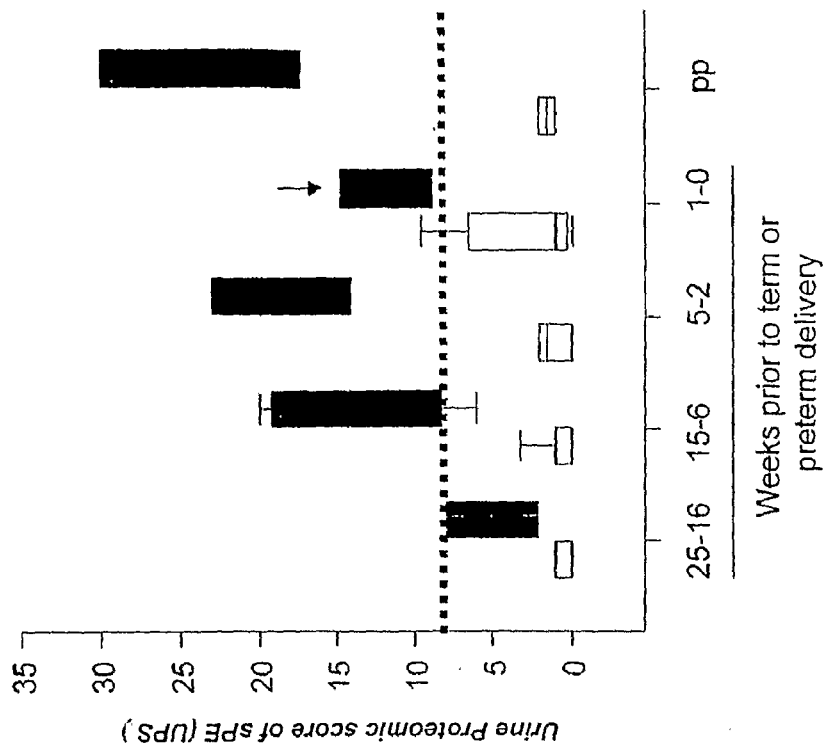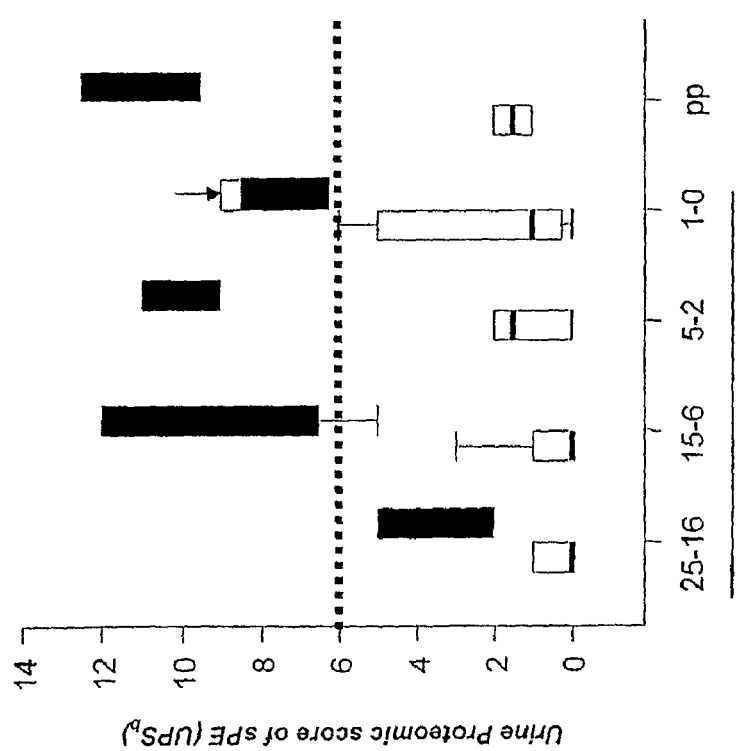
FIG. 5

Biomarkers matched to sequence of Serpina-1 [P01009]

```
    Signal peptide                                              P7
    |------------|  |----------------------------------------------------------|
  1 MPSSVSWGILLAGLCCLVPVSLAEDPQGDAAQKTDTSHHDQDHPTENKIVFALVNYIFFSAVLES        60
 61 LYRQLAHQSNSTNIFFSPVSIATAFAMLSLGTKADTHDEI LEGLNFNLTEIPEAQIHEGF           120
121 QELLRTLNQPDSQLQLTTGNGLFLSEGLKLVDKFLEDVKKLYHSEAFTVNFGDTEEAKKQ            180
181 INDYVEKGTQGKIVDLVKELDRDTVFALVNYIFFKGKWERPFEVKDTEEDFHVDQVTTV             240
241 KVPMMKRLGMFNIQHCKKLSSWVLLMKYLGNATAIFFLPDEGKLQHLENELTHDIITKFL            300
301 ENEDRRSASLHLPKLSITGTYDLKSVLGQLGITKVFSNGADLSGVTEEAPLKLSKAVHKA            360
                                                                P1, P2, P3
                                                          |----------------|
361 VLTIDEKGTEAAGAMFLEAI PMSIPPEVKFNKPFVFLMIEQNTKSPLFMGKVVNPTQK
```

FIG. 6

SEQUENCE LISTING

```
<160> NUMBER OF SEQ ID NOS: 10

<210> SEQ ID NO 1
<211> LENGTH: 21
<212> TYPE: PRT
<213> ORGANISM: Homo sapiens

<400> SEQUENCE: 1

Met Ile Glu Gln Asn Thr Lys Ser Pro Leu Phe Met Gly Lys Val Val
1               5                   10                  15

Asn Pro Thr Gln Lys
            20

<210> SEQ ID NO 2
<211> LENGTH: 21
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Oxidized methionine

<400> SEQUENCE: 2

Met Ile Glu Gln Asn Thr Lys Ser Pro Leu Phe Met Gly Lys Val Val
1               5                   10                  15

Asn Pro Thr Gln Lys
            20

<210> SEQ ID NO 3
```

-continued

```
<211> LENGTH: 21
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Oxidized methionine
<220> FEATURE:
<221> NAME/KEY: MISC_FEATURE
<222> LOCATION: (12)..(12)
<223> OTHER INFORMATION: Oxidized methionine

<400> SEQUENCE: 3

Met Ile Glu Gln Asn Thr Lys Ser Pro Leu Phe Met Gly Lys Val Val
1               5                   10                  15

Asn Pro Thr Gln Lys
            20

<210> SEQ ID NO 4
<211> LENGTH: 36
<212> TYPE: PRT
<213> ORGANISM: Homo sapiens

<400> SEQUENCE: 4

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser
            35

<210> SEQ ID NO 5
<211> LENGTH: 24
<212> TYPE: PRT
<213> ORGANISM: Homo sapiens

<400> SEQUENCE: 5

Asp Ala His Lys Ser Glu Val Ala His Arg Phe Lys Asp Leu Gly Glu
1               5                   10                  15

Glu Asn Phe Lys Ala Leu Val Leu
            20

<210> SEQ ID NO 6
<211> LENGTH: 26
<212> TYPE: PRT
<213> ORGANISM: Homo sapiens

<400> SEQUENCE: 6

Asp Ala His Lys Ser Glu Val Ala His Arg Phe Lys Asp Leu Gly Glu
1               5                   10                  15

Glu Asn Phe Lys Ala Leu Val Leu Ile Ala
            20                  25

<210> SEQ ID NO 7
<211> LENGTH: 418
<212> TYPE: PRT
<213> ORGANISM: Homo sapiens

<400> SEQUENCE: 7

Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
```

```
                35                  40                  45
Lys Ile Thr Pro Asn Leu Ala Glu Phe Ala Phe Ser Leu Tyr Arg Gln
 50                  55                  60
Leu Ala His Gln Ser Asn Ser Thr Asn Ile Phe Phe Ser Pro Val Ser
 65                  70                  75                  80
Ile Ala Thr Ala Phe Ala Met Leu Ser Leu Gly Thr Lys Ala Asp Thr
                 85                  90                  95
His Asp Glu Ile Leu Glu Gly Leu Asn Phe Asn Leu Thr Glu Ile Pro
            100                 105                 110
Glu Ala Gln Ile His Glu Gly Phe Gln Glu Leu Leu Arg Thr Leu Asn
            115                 120                 125
Gln Pro Asp Ser Gln Leu Gln Leu Thr Thr Gly Asn Gly Leu Phe Leu
130                 135                 140
Ser Glu Gly Leu Lys Leu Val Asp Lys Phe Leu Glu Asp Val Lys Lys
145                 150                 155                 160
Leu Tyr His Ser Glu Ala Phe Thr Val Asn Phe Gly Asp Thr Glu Glu
                165                 170                 175
Ala Lys Lys Gln Ile Asn Asp Tyr Val Glu Lys Gly Thr Gln Gly Lys
            180                 185                 190
Ile Val Asp Leu Val Lys Glu Leu Asp Arg Asp Thr Val Phe Ala Leu
            195                 200                 205
Val Asn Tyr Ile Phe Phe Lys Gly Lys Trp Glu Arg Pro Phe Glu Val
210                 215                 220
Lys Asp Thr Glu Glu Glu Asp Phe His Val Asp Gln Val Thr Thr Val
225                 230                 235                 240
Lys Val Pro Met Met Lys Arg Leu Gly Met Phe Asn Ile Gln His Cys
                245                 250                 255
Lys Lys Leu Ser Ser Trp Val Leu Leu Met Lys Tyr Leu Gly Asn Ala
            260                 265                 270
Thr Ala Ile Phe Phe Leu Pro Asp Glu Gly Lys Leu Gln His Leu Glu
            275                 280                 285
Asn Glu Leu Thr His Asp Ile Ile Thr Lys Phe Leu Glu Asn Glu Asp
290                 295                 300
Arg Arg Ser Ala Ser Leu His Leu Pro Lys Leu Ser Ile Thr Gly Thr
305                 310                 315                 320
Tyr Asp Leu Lys Ser Val Leu Gly Gln Leu Gly Ile Thr Lys Val Phe
                325                 330                 335
Ser Asn Gly Ala Asp Leu Ser Gly Val Thr Glu Glu Ala Pro Leu Lys
            340                 345                 350
Leu Ser Lys Ala Val His Lys Ala Val Leu Thr Ile Asp Glu Lys Gly
            355                 360                 365
Thr Glu Ala Ala Gly Ala Met Phe Leu Glu Ala Ile Pro Met Ser Ile
370                 375                 380
Pro Pro Glu Val Lys Phe Asn Lys Pro Phe Val Phe Leu Met Ile Glu
385                 390                 395                 400
Gln Asn Thr Lys Ser Pro Leu Phe Met Gly Lys Val Val Asn Pro Thr
                405                 410                 415
Gln Lys

<210> SEQ ID NO 8
<211> LENGTH: 609
<212> TYPE: PRT
<213> ORGANISM: Homo sapiens

<400> SEQUENCE: 8
```

```
Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
    370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
```

```
                            420             425             430
Val Arg Tyr Thr Lys Lys Val Pro Gln Val Ser Thr Pro Thr Leu Val
            435                 440                 445

Glu Val Ser Arg Asn Leu Gly Lys Val Gly Ser Lys Cys Cys Lys His
        450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
    530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
        595                 600                 605

Leu

<210> SEQ ID NO 9
<211> LENGTH: 22
<212> TYPE: PRT
<213> ORGANISM: Homo sapiens

<400> SEQUENCE: 9

Leu Met Ile Glu Gln Asn Thr Lys Ser Pro Leu Phe Met Gly Lys Val
1               5                   10                  15

Val Asn Pro Thr Gln Lys
            20

<210> SEQ ID NO 10
<211> LENGTH: 152
<212> TYPE: PRT
<213> ORGANISM: Homo sapiens

<400> SEQUENCE: 10

Gly Ser Lys Cys Cys Lys His Pro Glu Ala Lys Arg Met Pro Cys Ala
1               5                   10                  15

Glu Asp Tyr Leu Ser Val Val Leu Asn Gln Leu Cys Val Leu His Glu
            20                  25                  30

Lys Thr Pro Val Ser Asp Arg Val Thr Lys Cys Cys Thr Glu Ser Leu
        35                  40                  45

Val Asn Arg Arg Pro Cys Phe Ser Ala Leu Glu Val Asp Glu Thr Tyr
    50                  55                  60

Val Pro Lys Glu Phe Asn Ala Glu Thr Phe Thr Phe His Ala Asp Ile
65                  70                  75                  80

Cys Thr Leu Ser Glu Lys Glu Arg Gln Ile Lys Lys Gln Thr Ala Leu
                85                  90                  95

Val Glu Leu Val Lys His Lys Pro Lys Ala Thr Lys Glu Gln Leu Lys
            100                 105                 110
```

-continued

```
Ala Val Met Asp Asp Phe Ala Ala Phe Val Glu Lys Cys Cys Lys Ala
        115             120             125

Asp Asp Lys Glu Thr Cys Phe Ala Glu Glu Gly Lys Lys Leu Val Ala
    130             135             140

Ala Ser Gln Ala Ala Leu Gly Leu
145             150
```

URINARY PROTEOMIC BIOMARKER PATTERNS IN PREECLAMPSIA

RELATED APPLICATIONS

This application is a national phase filing under 35 U.S.C. §371 of International Application No. PCT/US2006/042585, filed Oct. 27, 2006, which claims the benefit of the filing date of U.S. provisional application having Ser. No. 60/730,888 and entitled "URINARY PROTEOMIC BIOMARKER PATTERNS IN PREECLAMPSIA", filed on Oct. 27, 2005. The entire teachings and contents of the referenced applications are incorporated herein by reference in their entirety.

FIELD OF THE INVENTION

The invention relates, in part, to the use of proteomic biomarkers to diagnose preeclampsia.

BACKGROUND OF THE INVENTION

Preeclampsia complicates 6-8% of pregnancies (Hauth, J. C. et al., Obstet Gynecol. 95(1):24-8, 2000) with an incidence in the US of 23.6 cases per 1000 deliveries in the US. (Samadi, A. R. et al., Obstet Gynecol. 87(4):557-63, 1996.) In recent statistics preeclampsia was classified as responsible for 20% of pregnancy-related maternal deaths (MacKay, A. P. et al., Paediatr Perinat Epidemiol. 19(3):206-14, 2005.) and the leading reason for a medically indicated preterm delivery (MIPTD) (Fronterhouse, W. et al., J Matern Fetal Med. 10(3): 162-5, 2001.) thus responsible for 10% of all premature births. (Fronterhouse, W. et al., J Matern Fetal Med. 10(3): 162-5, 2001.) Preeclampsia (PE) is defined new onset of elevated blood pressure with proteinuria after 20 weeks of gestation. (ACOG Committee on Practice Bulletins. Obstet Gynecol. 99(1):159-67, 2002.) It is considered severe (sPE) if blood pressure and proteinuria are increased substantially or symptoms of end-organ damage including fetal growth restriction occur. The course of severe preeclampsia is associated with a progressive deterioration of maternal condition and iatrogenic delivery remains the only definitive treatment. Management from the part of the caring physician consists of balancing the risks of immediate delivery of an immature fetus against the risks to both mother and child of a complication of preeclampsia. For this, the current approach is close monitoring of maternal and fetal status with delivery remaining the ultimate treatment. (Zamorski, M. A. & Green, L. A. Am Fam Physician 64: 263-70, 216, 2001.) The situation becomes further complicated for the caring physician when there is hypertension or a renal affect pre- or co-existing pregnancy and thus differentiating preeclampsia from similar clinical manifestations becomes very important from a managing standpoint.

From 1 to 5 percent of pregnant women have chronic hypertension (crHTN), defined as sustained hypertension that is present before conception or during the first 20 weeks of gestation. The rates are higher in obese, older, diabetic and black women. Chronic hypertension is a disease process that progresses slowly over years, in contrast to the usually more rapid course of preeclampsia over days. If uncomplicated by preeclampsia crHTN is usually a benign pregnancy complication for mother and child. On the other hand, crHTN predisposes to the risks of preeclampsia and abruptio placentae and thus to increased neonatal mortality and morbidity. The poor neonatal outcome among women with chronic hypertension is usually due to superimposed preeclampsia (spPE), but data regarding risk factors for preeclampsia and for adverse outcomes of pregnancy in women with chronic hypertension are sparse. The diagnosis of spPE is especially difficult in cases of preexisting proteinuria, chronic renal disease or other medical mimics such as systemic lupus flares. (Repke, J. T. J Reprod Med. 43(4):350-4, 1998; Williams, W. W. Jr. et al., N Engl J Med 353: 2590-600, 2005.) Because there is no sensitive or specific test for preeclampsia, the gold standard in such cases is renal biopsy, an invasive diagnostic test which needs to be performed in pregnancy, as a pre-pregnancy real biopsy is generally not predictive of renal outcome in pregnancy and change of histology in repeated biopsies was frequently observed. (Imbasciati, E. et al., Nephron. 36(1):46-51, 1984.)

To this date preeclampsia cannot be treated, except by delivery, and, therefore, efforts concentrate on correct case identification. Thus any preferably non-invasive test that can distinguish candidates for such mandated preterm delivery versus medical management would be helpful to practitioners.

SUMMARY OF THE INVENTION

The invention includes, in some aspects, methods and kits for identifying preeclampsia and other hypertensive disorders of pregnancy in a pregnant subject.

According to one aspect of the invention, methods of determining that a pregnant woman has preeclampsia or is at increased risk of developing preeclampsia are provided. The methods include (a) measuring a level of serpina-1 polypeptide and/or albumin polypeptide in a sample from the pregnant woman; and (b) comparing the level of serpina-1 polypeptide and/or albumin polypeptide in the sample with a reference value, wherein a higher level of serpina-1 polypeptide and/or albumin polypeptide in the sample relative to the reference value indicates that the pregnant woman has preeclampsia or is at increased risk of developing preeclampsia. In some embodiments, the sample is a urine sample. In certain embodiments, the serpina-1 polypeptide or albumin polypeptide level is measured using an immunological assay. In some embodiments, the immunological assay is an ELISA assay. In some embodiments, the serpina-1 polypeptide and/or albumin polypeptide is measured using a protein chip assay. In certain embodiments, the serpina-1 polypeptide and/or albumin polypeptide level is measured by surface-enhanced laser desorption/ionization (SELDI). In some embodiments, the serpina-1 polypeptide and/or albumin polypeptide is polymerized serpina-1 polypeptide or polymerized albumin polypeptide respectively. In some embodiments, the serpina-1 polypeptide comprises the amino acid sequence set forth as MIEQNTKSPLFMGKVVNPTQK (SEQ ID NO:1). In certain embodiments, the serpina-1 polypeptide comprises the amino acid sequence set forth as $M_{ox}$IEQNTKSPLFMGKVVNPTQK (SEQ ID NO:2). In some embodiments, the serpina-1 polypeptide comprises the amino acid sequence set forth as $M_{ox}$IEQNTKSPLFM$_{ox}$GKVVNPTQK (SEQ ID NO:3). In some embodiments, the serpina-1 polypeptide comprises the amino acid sequence set forth as EDPQGDAAQKTDTSHHDQDHPTFNKITPNLAEFAFS (SEQ ID NO:4). In certain embodiments, the serpina-1 polypeptide comprises the amino acid sequence set forth as EDPQGDAAQKTDTSHHDQDHPTFNKITPNLAEFAFS (SEQ ID NO:4). In some embodiments, the albumin polypeptide comprises the amino acid sequence set forth as DAHKSEVAHRFKDLGEENFKALVL (SEQ ID NO:5). In some embodiments, the albumin polypeptide comprises the amino acid sequence set forth as DAHKSEVAHRFKDLGEENFKALVLIA (SEQ ID NO:6). In some embodiments, the albumin polypeptide is a fragment of the amino acid sequence set forth as GSKCCKHPEAKRMPCAEDYLSVVLNQLCVLHEKTPVSDRVTKCCTESLVNRRPCFSAL EVDETYVPKEFNAETFTFHADICTLSEK-ERQIKKQTALVELVKHKPKATKEQLKAVMD DFAAFVEKCCKADDKETCFAEEGKKLVAASQAALGL (SEQ ID NO:10). According to another aspect of the invention, methods for identifying onset, progression, or regression of preeclampsia in a pregnant woman are provided. The methods include (a) measuring a level of serpina-1 polypeptide and/or albumin polypeptide in a first sample obtained from the pregnant woman; and (b) measuring a level of serpina-1 polypeptide and/or albumin polypeptide in a second sample obtained from the same pregnant woman, wherein the second sample is obtained at a time subsequent to the time the first sample is obtained, wherein an increase in the serpina-1 polypeptide and/or albumin polypeptide level in the second sample relative to the serpina-1 polypeptide and/or albumin polypeptide level in the first sample identifies onset or progression of preeclampsia in the subject and a decrease in the serpina-1 polypeptide and/or albumin polypeptide level in the second sample relative to the serpina-1 polypeptide and/or albumin polypeptide level in the first sample identifies regression of preeclampsia in the subject. In certain embodiments, the serpina-1 polypeptide and/or albumin polypeptide is measured using an immunological assay. In some embodiments, the serpina-1 polypeptide and/or albumin polypeptide is measured using a protein chip assay. In some embodiments, the serpina-1 polypeptide and/or albumin polypeptide level is measured by seldi. In certain embodiments, the serpina-1 polypeptide is a polymerized serpina-1 polypeptide and the albumin polypeptide is a polymerized albumin polypeptide. In some embodiments, the serpina-1 polypeptide comprises the amino acid sequence set forth as MIEQNTKSPLFMGKVVNPTQK (SEQ ID NO:1). In some embodiments, the serpina-1 polypeptide comprises the amino acid sequence set forth as $M_{ox}$IEQNTKSPLFMGKVVNPTQK (SEQ ID NO:2). In some embodiments, the serpina-1 polypeptide comprises the amino acid sequence set forth as $M_{ox}$IEQNTKSPLFM$_{ox}$GKVVNPTQK (SEQ ID NO:3). In certain embodiments, the serpina-1 polypeptide comprises the amino acid sequence set forth as EDPQGDAAQKTDTSHHDQDHPTFNKITPNLAEFAFS (SEQ ID NO:4). In some embodiments, the serpina-1 polypeptide comprises the amino acid sequence set forth as EDPQGDAAQKTDTSHHDQDHPTFNKITPNLAEFAFS (SEQ ID NO:4). In some embodiments, the albumin polypeptide comprises the amino acid sequence set forth as DAHKSEVAHRFKDLGEENFKALVL (SEQ ID NO:5). In certain embodiments, the albumin polypeptide comprises the amino acid sequence set forth as DAHKSEVAHRFKDLGEENFKALVLIA (SEQ ID NO:6). In some embodiments, the albumin polypeptide is a fragment of the amino acid sequence set forth as GSKCCKHPEAKRMPCAEDYLSVVLNQLCVLHEKTPVSDRVTKCCTESLVNRRPCFSAL EVDETYVPKEFNAETFTFHADICTLSEKERQIKKQTALVELVKHKPKATKEQLKAVMD DFAAFVEKCCKADDKETCFAEEGKKLVAASQAALGL (SEQ ID NO:10).

According to yet another aspect of the invention, methods of assessing efficacy of a treatment for preeclampsia in a pregnant woman are provided. The methods include measuring the level of serpina-1 polypeptide and/or albumin polypeptide in a first sample obtained from the pregnant woman before the treatment for preeclampsia; (b) measuring the level of serpina-1 polypeptide and/or albumin polypeptide in a second sample from the same pregnant woman after the treatment for preeclampsia; and (c) comparing the level determined in (a) with the level determined in (b), wherein a decrease in the serpina-1 polypeptide and/or albumin polypeptide level in the second sample relative to the serpina-1 polypeptide and/or albumin polypeptide level in the first sample indicates the treatment for preeclampsia is effective and wherein no reduction in the serpina-1 polypeptide and/or albumin polypeptide level in the second sample relative to the serpina-1 polypeptide and/or albumin polypeptide level in the first sample indicates the treatment for preeclampsia is not effective. In some embodiments, the serpina-1 polypeptide and/or albumin polypeptide is measured using an immunological assay. In some embodiments, the serpina-1 polypeptide and/or albumin polypeptide is measured using a protein chip assay. In certain embodiments, the serpina-1 polypeptide and/or albumin polypeptide level is measured by seldi. In some embodiments, the serpina-1 polypeptide is polymerized serpina-1 polypeptide and the albumin polypeptide is polymerized albumin polypeptide. In certain embodiments, the serpina-1 polypeptide comprises the amino acid sequence set forth as MIEQNTKSPLFMGKVVNPTQK (SEQ ID NO:1). In some embodiments, the serpina-1 polypeptide comprises the amino acid sequence set forth as $M_{ox}$IEQNTKSPLFMGKVVNPTQK (SEQ ID NO:2). In some embodiments, the serpina-1 polypeptide comprises the amino acid sequence set forth as $M_{ox}$iEQNTKSPLF-$M_{ox}$GKVVNPTQK (SEQ ID NO:3). In some embodiments, the serpina-1 polypeptide comprises the amino acid sequence set forth as EDPQGDAAQKTDTSHHDQDHPTFNKITPNLAEFAFS (SEQ ID NO:4). In certain embodiments, the serpina-1 polypeptide comprises the amino acid sequence set forth as EDPQGDAAQKTDTSHHDQDHPTFNKITPNLAEFAFS (SEQ ID NO:4). In some embodiments, the albumin polypeptide comprises the amino acid sequence set forth as DAHKSEVAHRFKDLGEENFKALVL (SEQ ID NO:5). In some embodiments, the albumin polypeptide comprises the amino acid sequence set forth as DAHKSEVAHRFKDLGEENFKALVLIA (SEQ ID NO:6). In certain embodiments, the albumin polypeptide is a fragment of the amino acid sequence set forth as GSKCCKHPEAKRMPCAEDYLSVVLNQLCVLHEKTPVSDRVTKCCTESLVNRRPCFSAL EVDETYVPKEFNAETFTFHADICTLSEKERQIKKQTALVELVKHKPKATKEQLKAVMD DFAAFVEKCCKADDKETCFAEEGKKLVAASQAALGL (SEQ ID NO:10).

According to yet another aspect of the invention, kits are provided. Kits may include (a) an agent that binds to a serpina-1 polypeptide; and/or (b) an agent that binds to an albumin polypeptide; and optionally, (c) instructions to measure serpina-1 polypeptide and/or albumin polypeptide by contacting a sample with the serpina-1 binding agent and detecting the serpina-1 polypeptide retained by the agent and/or contacting the sample with the albumin binding agent and detecting the albumin polypeptide retained by the agent. In some embodiments, the agent is an antibody that specifically binds to serpina-1 polypeptide and/or an antibody that specifically binds to albumin polypeptide. In some embodiments, the serpina-1 polypeptide comprises the amino acid sequence set forth as MIEQNTKSPLFMGKVVNPTQK (SEQ ID NO:1). In certain embodiments, the serpina-1 polypeptide comprises the amino acid sequence set forth as $M_{ox}$IEQNTKSPLFMGKVVNPTQK (SEQ ID NO:2). In some embodiments, the serpina-1 polypeptide comprises the amino acid sequence set forth as $M_{ox}$IEQNTKSPLF-$M_{ox}$GKVVNPTQK (SEQ ID NO:3). In some embodiments, the serpina-1 polypeptide comprises the amino acid sequence set forth as EDPQGDAAQKTDTSHHDQDHPTFNKITPNLAEFAFS (SEQ ID NO:4). In some embodiments, the serpina-1 polypeptide comprises the amino acid sequence set forth as EDPQGDAAQKTDTSHHDQDHPTFNKITP-NLAEFAFS (SEQ ID NO:4). In certain embodiments, the albumin polypeptide comprises the amino acid sequence set forth as DAHKSEVAHRFKDLGEENFKALVL (SEQ ID NO:5). In some embodiments, the albumin polypeptide comprises the amino acid sequence set forth as DAHKSEVAHR-FKDLGEENFKALVLIA (SEQ ID NO:6). In some embodiments, the albumin polypeptide is a fragment of the amino acid sequence set forth as GSKCCKHPEAKRMPCAE-DYLSVVLNQLCVLHEKTPVSDRVTKC-CTESLVNRRPCFSAL EVDETYVPKEFNAETFTFHAD-ICTLSEKERQIKKQTALVELVKHKPKATKEQLKAVMD DFAAFVEKCCKADDKETCFAEEGKKLVAASQAALGL (SEQ ID NO:10). In certain embodiments, the agent is immobilized. In some embodiments, the kit also includes a wash solution that selectively allows retention of the bound serpina-1 polypeptide and/or albumin polypeptide to the agent as compared with other polypeptides after washing. In some embodiments, the kit also includes a second agent that binds to a second biomarker for preeclampsia. In certain embodiments, the second biomarker is placental growth factor (PlGF) or sFlt-1.

According to yet another aspect of the invention, methods of identifying a compound to treat preeclampsia are provided. The methods include (a) administering a candidate compound to a pregnant subject; (b) comparing a level of serpina-1 polypeptide and/or albumin polypeptide in a test sample obtained from the subject with the level of serpina-1 polypeptide and/or albumin polypeptide in a control sample, wherein if the serpina-1 and/or albumin level is lower in the test sample than in the control sample, the candidate compound is a compound that treats preeclampsia. In some embodiments, the serpina-1 polypeptide and/or albumin polypeptide level is measured using an immunological assay. In some embodiments, the serpina-1 polypeptide and/or albumin polypeptide is measured using a protein chip assay. In certain embodiments, the serpina-1 polypeptide and/or albumin polypeptide level is measured by seldi. In some embodiments, the serpina-1 polypeptide is polymerized serpina-1 polypeptide and/or the albumin polypeptide is polymerized albumin polypeptide. In some embodiments, the serpina-1 polypeptide comprises the amino acid sequence set forth as MIEQNTKSPLFMGKVVNPTQK (SEQ ID NO:1). In certain embodiments, the serpina-1 polypeptide comprises the amino acid sequence set forth as $M_{ox}$IEQNTKSPLFMGKV-VNPTQK (SEQ ID NO:2). In some embodiments, the serpina-1 polypeptide comprises the amino acid sequence set forth as $M_{ox}$IEQNTKSPLFM$_{ox}$GKVVNPTQK (SEQ ID NO:3). In some embodiments, the serpina-1 polypeptide comprises the amino acid sequence set forth as EDPQGDAAQKTDTSHHDQDHPTFNKITPNLAEFAFS (SEQ ID NO:4). In certain embodiments, the serpina-1 polypeptide comprises the amino acid sequence set forth as EDPQGDAAQKTDTSHHDQDHPTFNKITPNLAEFAFS (SEQ ID NO:4). In some embodiments, the albumin polypeptide comprises the amino acid sequence set forth as DAHK-SEVAHRFKDLGEENFKALVL (SEQ ID NO:5). In some embodiments, the albumin polypeptide comprises the amino acid sequence set forth as DAHKSEVAHRFKDLGEEN-FKALVLIA (SEQ ID NO:6). In certain embodiments, the albumin polypeptide is a fragment of the amino acid sequence set forth as GSKCCKHPEAKRMPCAEDYLSVVLNQL-CVLHEKTPVSDRVTKCCTESLVNRRPCFSAL EVDETYVPKEFNAETFTFHADICTLSEK-ERQIKKQTALVELVKHKPKATKEQLKAVMD DFAAFVEKCCKADDKETCFAEEGKKLVAASQAALGL (SEQ ID NO:10). In some embodiments, the subject is a human. In certain embodiments, the subject is pregnant.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 5: UPSb (FIG. 5A) and UPSr (FIG. 5B)) scores for a group of 11 patients followed longitudinally during pregnancy before clinically manifest preeclampsia. Black bars represent values from patients that ultimately developed preeclampsia or superimposed preeclampsia (n=3). Open bars represent patients who had a normal course of their pregnancy (n=8). On the x axis are the time periods in weeks prior to each patient's delivery date (time 0). pp=postpartum. The arrow indicates the time-point where patients manifested clinical signs or symptoms of preeclampsia requiring a medically indicated delivery. The data is presented as percentiles with median. The ends of the boxes define the $25^{th}$ and $75^{th}$ percentiles, the line inside the box defines the median and the whiskers show the largest and smallest values. Two-way ANOVA: $p<0.01$ for both time periods and outcome.

FIG. 6 provides the sequence of serpina-1 (SEQ ID NO:7; Genbank Accession No. P01009) and indicates with shading the regions that include P7 and P1-3 fragments.

DETAILED DESCRIPTION

Figure 1:
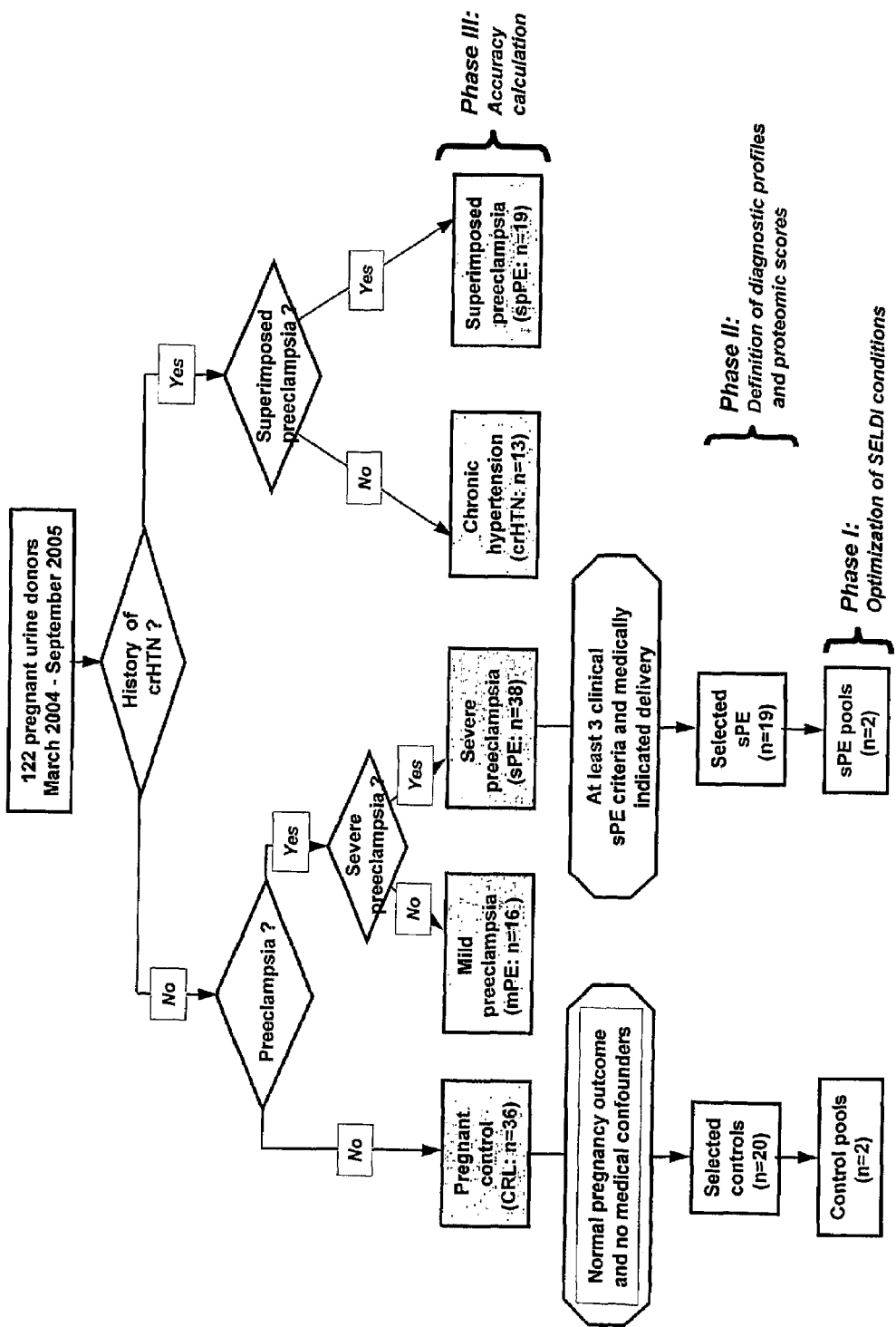
FIG. 1 is a diagram of a study flow chart and distribution of urine samples used to extract proteomic profiles diagnostic for severe preeclampsia. Abbreviations: sPE: severe preeclampsia; mPE: mild preeclampsia; crHTN: chronic hypertension; CRL: pregnant control.

Preeclampsia is a condition that develops in the second half of pregnancy and is associated with significant maternal and fetal morbidity and mortality. Because there is no effective screening test to diagnose or assess the risk of developing preeclampsia and associated hypertensive disorders, pregnant women cannot receive effective monitoring or treatment until long after complications associated with the disorders, including increased blood pressure and proteinuria, have developed. In addition, pregnant women with little to no risk of developing preeclampsia or associated hypertensive disorders must undergo unnecessary testing for symptoms throughout their pregnancy because there is no effective means by which caregivers may exclude them from risk in the early stages of pregnancy.

As used herein, "preeclampsia" is defined according to well-established criteria, such as a blood pressure of at least 140/90 mm Hg and urinary excretion of at least 0.3 grams of protein in a 24-hour urinary protein excretion (or at least +1 or greater on dipstick testing), each on two occasions 4-6 hours apart. As used herein, "severe preeclampsia" is also defined in accordance with established criteria, as a blood pressure of at least 160/110 mm Hg on at least 2 occasions 6 hours apart and greater than 5 grams of protein in a 24-hour urinary protein excretion or persistent +3 proteinuria on dipstick testing. Severe preeclampsia may include HELLP syndrome (hemolysis, elevated liver enzymes, low platelet count). Other elements of severe preeclampsia may include in-utero growth restriction (IUGR) in less than the 10% percentile according to the US demographics, persistent neurologic symptoms (headache, visual disturbances), epigastric pain, oliguria (less than 500 mL/24 h), serum creatinine greater than 1.0 mg/dL, elevated liver enzymes (greater than two times normal), thrombocytopenia (<100,000 cells/μL).

In certain aspects, the present invention provides biomarkers for preeclampsia and methods that are useful for determining a preeclampsia status of a pregnant woman by measuring one or more of the biomarkers. The measurement of biomarkers in patient samples, such as urine samples, provides information useful to diagnose preeclampsia in women with chronic hypertension, as well as in women without chronic hypertension. Specifically, biomarkers of the present invention were identified by comparing mass spectra of urine samples obtained from two groups of pregnant subjects (women): subjects with preeclampsia and normal subjects. The subjects were diagnosed according to standard clinical criteria.

Biomarkers shown to be associated with preeclampsia may be used in the present methods. In certain embodiments of the invention, one or more biomarkers (e.g., polypeptides) in urine that are present at higher levels in women with preeclampsia than in pregnant women without preeclampsia are assessed. An increased level of such a biomarker(s) in urine indicates that the pregnant woman has preeclampsia or is at risk of developing preeclampsia. As used herein, the term "polypeptide" refers to a polymer of amino acids, and not to a specific length. Thus, peptides, oligopeptides and proteins are included within the definition of polypeptide.

A biomarker may be a serpina-1 polypeptide. As used herein the term "serpina-1 polypeptide" refers to full-length serpina-1 polypeptide and also to a polypeptide that is a fragment of full-length serpina-1 polypeptide. Serpina-1 polypeptides can be used in methods and kits of the invention. Examples of serpina-1 biomarkers are set forth herein as SEQ ID NOs: 1-4. A biomarker of the invention may also be an albumin polypeptide. As used herein, the term "albumin polypeptide" is meant to refer to full-length albumin polypeptide and also refers to a polypeptide that is a fragment of full-length albumin polypeptide. Albumin polypeptides can be used in methods and kits of the invention. Examples of albumin polypeptide biomarkers are set forth herein as SEQ ID NOs:5 and 6.

In certain aspects, the present invention relates to methods of detecting and/or measuring serpina-1 polypeptides and/or albumin polypeptides in a sample from a subject (e.g., urine) for determining preeclampsia status. Applicants have demonstrated, using proteomic technology (SELDI-TOF mass spectroscopy) coupled with standard molecular and biochemical identification assays, that women with preeclampsia have higher levels of serpina-1 polypeptides and/or albumin polypeptides in their urine and other fluids and tissues, than do women without preeclampsia.

Serpina-1 has been previously identified as a serine protease inhibitor, and is also known as alpha 1 antitrypsin. The amino acid sequence of the most common allele of full-length serpina-1 polypeptide is set forth as SEQ ID NO:7 and has Genbank Accession No. P01009. It will be understood that serpina-1 polypeptides encoded by alternative alleles of serpina-1 may also be used to detect the presence of preeclampsia in subjects. For example, serpina-1 polypeptides encoded by M1A, M2, and/or M3 alleles of serpina-1 may be used in methods of the invention to diagnose and/or assess preeclampsia in subjects. Serpina-1 polypeptides are synthesized in the liver and trophoblast and are present in multiple forms that are unrelated to serpina-1's antiproteolytic activity. Serpina-1 polypeptide is highly susceptible to oxidation and intensive oxidative stress induces Serpina-1 oxidation. A polypeptide that is a fragment at the C-terminus of full-length Serpina-1 polypeptide induces oxidative burst and neutrophil chemotaxis in vitro. The wild-type, full-length amino acid sequence of albumin is set forth herein as SEQ ID NO:8 and has Genbank Accession No. P02768. It will be understood that albumin polypeptides encoded by alternative alleles of albumin may also be used to detect the presence of preeclampsia in subjects according to methods of the invention.

Homologs and alleles of serpina-1 encoding DNA and albumin-encoding DNA, and the polypeptides they encode, are understood to be encompassed by methods and kits of the invention. The skilled artisan is familiar with the methodology for screening cells and libraries for expression of homolog and allelic molecules that then are routinely isolated, followed by isolation of the pertinent nucleic acid molecule and sequencing. In addition, polypeptides encoded by known alleles of serpina-1 and albumin may be used in the methods of the invention to diagnose and assess preeclampsia in a subject.

In general, homologs and alleles typically will share at least 80% nucleotide identity and/or at least 80% amino acid identity to the wild-type serpina-1 or albumin gene sequence and the serpina-1 and albumin polypeptide sequences, which are provided herein as SEQ ID NOs: 14 and 15, and in some instances will share at least 81%, 82%, 83%, 84%, 85%, 86%, 87%, 88%, 89%, 90%, 91%, 92%, 93%, 94%, 95%, 96%, 97%, 98%, or 99, 99.5% nucleotide identity and/or at least 81%, 82%, 83%, 84%, 85%, 86%, 87%, 88%, 89%, 90%, 91%, 92%, 93%, 94%, 95%, 96%, 97%, 98%, or 99, 99.5% amino acid identity. The percent identity can be calculated using various publicly available software tools developed by NCBI (Bethesda, Md.) that can be obtained through the internet (ftp:/ncbi.nlm.nih.gov/pub/). Exemplary tools include the BLAST system available at http://www.ncbi.nlm.nih.gov, which uses algorithms developed by Altschul et al. (*Nucleic Acids Res.* 25:3389-3402, 1997). Pairwise and ClustalW alignments (BLOSUM30 matrix setting) as well as Kyte-Doolittle hydropathic analysis can be obtained using the MacVector sequence analysis software (Oxford Molecular Group). Watson-Crick complements of the foregoing nucleic acid molecules also are embraced by the invention.

As used herein, the term "biomarker" refers to an organic biomolecule, preferably, a polypeptide that is differentially present in a sample taken from a subject having preeclampsia as compared to a comparable sample taken from a subject, referred to as a "normal" subject, who does not have preeclampsia. A biomarker is differentially present in samples from subjects with preeclampsia, if it is present at an elevated level in the subject with preeclampsia, as compared to samples from normal subjects. Examples of biomarkers of the invention are serpina-1 polypeptides and albumin polypeptides that may be present in a sample from a subject.

Described herein are methods, kits, and compositions related to the detection and/or monitoring of the levels of biomarkers for preeclampsia, specifically serpina-1 polypeptides and albumin polypeptides, in samples (e.g., urine samples) obtained from pregnant women and the relationship between such levels and the likelihood that a pregnant woman will develop a hypertensive disorder, such as preeclampsia during the progression of pregnancy. The "progression of pregnancy" refers to the various stages or phases of pregnancy, including pregnancy throughout each trimester and during the transition from one trimester to the next. The progression of pregnancy includes the course of pregnancy in both normal pregnancies and pregnancies in which a hypertensive disorder develops. The term "normal pregnancy" refers to a pregnancy that is not complicated by and in which the woman does not develop preeclampsia.

In methods disclosed herein, a pregnant women may be diagnosed as having or having an increased risk for developing any of the following hypertensive disorders: preeclampsia, eclampsia, mild preeclampsia, chronic hypertension, EPH gestosis, gestational hypertension, superimposed preeclampsia (including preeclampsia superimposed on chronic hypertension, chronic nephropathy or lupus), HELLP syndrome (hemolysis, elevated liver enzymes, low platelet count) or nephropathy. Although this invention is described with respect to pregnant women, methods described herein may also be utilized to assess the risk to non-pregnant women of developing hypertensive disorders during pregnancy.

Methods and compositions described herein permit assessment and/or monitoring risk in a pregnant woman of developing preeclampsia by detecting and/or monitoring levels of biomarkers (e.g., serpina-1 polypeptides and/or albumin polypeptides) in a sample obtained from the pregnant woman. This can be carried out by obtaining a urine sample and detecting levels of biomarkers of the invention, as described herein, at varied times as the pregnancy progresses. Resulting values may also be compared to a control or known (pre-established) standard. As used herein, the terms "appropriate standard" or "control" refers to the levels of the biomarker in urine obtained from a reference subject. The appropriate standard concentration can be determined from urine samples obtained from pregnant women with normal pregnancies or from pregnant women who have a confirmed hypertensive disorder, such as preeclampsia (reference or control subjects). In some embodiments of the invention, samples that form the basis of an appropriate standard are obtained from the reference subject who, when the sample is obtained, is in the week of pregnancy corresponding to that week of pregnancy the test subject is in when the test sample is obtained. Samples may be obtained and analyzed at the same time as urine samples are obtained from test subjects. Alternatively, serpina-1 and albumin polypeptide levels may be determined prospectively or retrospectively to the assessment of the urine sample obtained from a test subject using statistical studies with routine experimentation. Standard serpina-1 and albumin polypeptide levels can be determined by a person having ordinary skill in the art using well known methods.

Assays to detect biomarkers of the invention, as described herein, involve determining the presence or absence of and/or measuring levels of serpina-1 polypeptides and/or albumin polypeptides. The presence and/or level of serpina-1 and albumin polypeptides can be determined in a number of ways when carrying out the various methods of the invention. In one particularly important measurement, serpina-1 and/or albumin polypeptides are measured in relation to a control level of serpina-1 and/or albumin polypeptides in a fluid or tissue sample. One possible measurement of levels of serpina-1 and/or albumin polypeptides is a measurement of absolute level of serpina-1 and/or albumin polypeptides. This could be expressed, for example, in serpina-1 and/or albumin polypeptides per unit of tissue or volume of urine or other fluid sample. Another measurement of the level of serpina-1 and/or albumin polypeptides is a measurement of changes in levels of serpina-1 and/or albumin polypeptides over time. This may be expressed in an absolute amount or may be expressed in terms of a percentage increase or decrease over time.

Antibodies or antigen-binding fragments known in the art, mass spectrometry (e.g., SELDI), protein chip techniques, and/or other methods of determining levels of serpina-1 and/or albumin polypeptides in a sample may be used in diagnostic methods of the invention. Known antibodies that may be useful in methods of the invention include, but are not limited to antibodies that specifically bind serpina-1 polypeptides such as A1AT antibody (Affinity Biologicals, Ancaster, Canada) and antibodies that specifically bind albumin polypeptides. Those of ordinary skill in the art will recognize additional antibodies that specifically bind serpina-1 polypeptides and albumin polypeptides that can be used in methods and kits of the invention. Antibodies and other means as disclosed herein may be used to detect the presence of and/or to quantitate the level of serpina-1 and/or albumin polypeptides per unit of cells, per volume of urine.

Importantly, the presence and/or levels of serpina-1 and/or albumin polypeptides can be determined using a suitable method and are advantageously compared to controls according to the invention. A control may be a predetermined value, which can take a variety of forms. It can be a single cut-off value, such as a median or mean. It can be established based upon comparative groups, such as in groups having normal amounts of serpina-1 and/or albumin polypeptides and groups having abnormal amounts of serpina-1 and/or albumin polypeptides. Another example of comparative groups may be groups having preeclampsia symptoms or diagnosed preeclampsia and groups without preeclampsia symptoms or diagnosed preeclampsia. Another comparative group may be a group with a personal or family history of hypertension or preeclampsia and a group without such a personal or family history. In some embodiments, a comparative group includes women at the same state of progression of pregnancy as a test subject. A predetermined value can be arranged, for example, where a tested population is divided equally (or unequally) into groups, such as a low-risk group, a medium-risk group and a high-risk group or into quadrants or quintiles, the lowest quadrant or quintile being individuals with the lowest risk (e.g. of preeclampsia) and lowest amounts of serpina-1 and/or albumin polypeptides and the highest quadrant or quintile being individuals with the highest risk (e.g. of preeclampsia) and highest amounts of serpina-1 and/or albumin polypeptides.

The predetermined value will depend upon the particular population selected. For example, an apparently healthy population will have a different 'normal' range than will a population that is known to have a condition related to abnormal serpina-1 and/or albumin polypeptides levels. Accordingly, the predetermined value selected may take into account the category into which an individual falls. Appropriate ranges and categories can be selected with no more than routine experimentation by those of ordinary skill in the art. As used herein, "abnormal" means not normal as compared to a control. By abnormally high it is meant high relative to a selected control. Typically the control will be based on apparently healthy normal individuals in an appropriate age bracket and pregnancy status.

It will be understood that a control according to the invention may, in addition to being a predetermined value, may be serpina-1 and/or albumin polypeptide levels obtained from the same subject at a different point in time, e.g., prior to pregnancy or at a different point in the subject's progression of pregnancy.

As mentioned above, it is also possible to use detection methods of the invention to characterize serpina-1 and/or albumin polypeptides levels by monitoring changes in levels of serpina-1 and/or albumin polypeptides over time. For example, it is expected that an increase in serpina-1 and/or albumin polypeptides levels correlates with an increase of the occurrence of preeclampsia in a subject. Accordingly one can monitor levels of serpina-1 and/or albumin polypeptides in a subject over time to determine if there is a change in preeclampsia status in a subject during pregnancy. Changes in levels of serpina-1 and/or albumin polypeptides greater than 0.1% may indicate an abnormality. Preferably, increases in serpina-1 and/or albumin polypeptides levels, which indicate an abnormality, are increases of greater than 0.2%, greater than 0.5%, greater than 1.0%, 2.0%, 3.0%, 4.0%, 5.0%, 7.0%, 10%, 15%, 20%, 25%, 30%, 40%, 50%, or more. Increases in the level of serpina-1 and/or albumin polypeptides over time may indicate a change in preeclampsia status in a subject.

Methods of detecting levels of serpina-1 and/or albumin polypeptides, including those provided herein and other art-recognized methods, may also be used in diagnostic methods to determine the effectiveness of a treatment for preeclampsia. "Evaluation of treatment" as used herein, means the comparison of a woman's levels of serpina-1 and/or albumin polypeptides measured in samples obtained from the woman at different sample times, preferably at least one day apart. In some embodiments, the time to obtain the second sample from the woman is at least 5, 10, 20, 30, 40, 50, minutes after obtaining the first sample from the subject. In certain embodiments, the time to obtain the second sample from the woman is at least 1, 2, 3, 4, 5, 6, 7, 8, 9, 10, 11, 12, 13, 14, 15, 16, 17, 18, 19, 20, 21, 22, 23, 24, 36, 48, 72, 96, 120, 168, or more hours (including all times in between) after obtaining the first sample from the woman.

Methods of the invention may be used to allow comparison of levels of serpina-1 and/or albumin polypeptides in two or more samples, taken at different times, which may be used to detect the status of preeclampsia in a subject and allows evaluation of a preeclampsia treatment as well as evaluation of a treatment to prevent the onset of preeclampsia in a subject. The comparison of a subject's levels of serpina-1 and/or albumin polypeptides measured in samples obtained at different times and/or on different days provides a measure of preeclampsia status that can be used to determine the effectiveness of any treatment for preeclampsia and for preeclampsia prevention in a subject.

As will be appreciated by those of ordinary skill in the art, evaluation of a treatment also may be based upon an evaluation of the symptoms or clinical end-points of preeclampsia. Thus, methods of the invention are useful for determining the onset, progression or regression of a condition that is characterized by an increase in level of serpina-1 and/or albumin polypeptides in a pregnant subject. In some instances, methods of the invention can be used to detect levels of serpina-1 and/or albumin polypeptides in subjects diagnosed as having preeclampsia. In other instances, methods of the invention can be used to obtain measurements that represent the diagnosis of preeclampsia in a subject. In some instances, a subject may be already be undergoing drug therapy for preeclampsia, while in other instances a subject may be without present preeclampsia therapy.

In this aspect of the invention, the type of treatment for preeclampsia selected may be based, in part, upon selecting subjects who have abnormally high levels of serpina-1 and/or albumin polypeptides. Treatments may include administration of a particular type of drug, or an activity change, or a dietary change, that may be based at least in part on the presence or absence of an indication of preeclampsia (e.g., detection of a level of serpina-1 and/or albumin polypeptides in the subject). Such subjects may already be receiving a drug for treating preeclampsia. It may be appropriate according to the invention to alter a therapeutic regimen for a subject, based upon the measurement of the level of serpina-1 and/or albumin polypeptides using a method set forth herein. This can be understood in connection with treatment of preeclampsia. A subject may be free of any present treatment for preeclampsia and monitoring of serpina-1 and/or albumin polypeptides levels may allow selection of the most efficacious treatment regimen.

A urine sample that can be assessed by the methods of the present invention is one that contains sufficient levels of biomarker(s) of interest for detection by the assessment techniques described herein. In particular, the urine sample must have measurable levels of at least one serpina-1 polypeptide and/or albumin polypeptide, as applicable to the assessment technique utilized. Urine samples may be analyzed immediately after collection or at a later time, provided that, when analyzed, the sample contains detectable levels of the biomarker(s) of interest. For example, urine samples may be frozen at −70° C. and/or mixed, combined, or stored in a container pretreated with agents that stabilize or preserve the biomarker(s) of interest. In a preferred embodiment, a urine sample is collected from the first morning void.

The presence and/or level of a biomarker that is useful in a method of the present invention may be assessed by any of a wide variety of well-known methods for detecting expression of a transcribed molecule or its corresponding polypeptide or polypeptide fragment. Non-limiting examples of such methods include immunological methods for detection of secreted proteins, protein purification methods, protein function or activity assays, nucleic acid hybridization methods, nucleic acid reverse transcription methods, and nucleic acid amplification methods. In one embodiment, a level of a biomarker is assessed using an ELISA assay, SELDI-TOF mass spectrometry, etc.

In certain embodiments, the invention comprises treating a urine sample(s) from a pregnant subject with one or more stabilizing agent(s) and/or pre-treating the container used for collection of such urine sample(s) with one or more stabilizing agent prior to measuring the levels of biomarkers. The term "stabilizing agent" refers to one or more molecules, such as polypeptides or nucleic acids, that can be used to prevent the degradation of the biomarkers. In one embodiment, the stabilizing agent is a protease inhibitor, including any of 4-(2-Aminoethyl) benzenesulphonyl fluoride (AEBSF) and Pefabloc SC, Antipain and Antipain-dihydrochloride, Aprotinin, Benzamidine and Benzamidine hydrochloride, Bestatin, Chymostatin, E-64 (L-trans-epoxysuccinyl-leucylamide-(4-guanido)-butane or N—[N-(L-trans-carboxyoxiran-2-carbonyl)-L-leucyl]-agmatine), Ethylenediaminetetraacetic acid and its sodium salt (EDTA-Na2), Leupeptin, Ethylmaleimide, Pepstatin and Pepstatin A, Phosphoramidon, Sodium azide, Trypsin inhibitor or ε-aminocaproic acid.

Applicants have demonstrated that serpina-1 polypeptides and albumin polypeptides are significantly increased in pregnant women with preeclampsia (e.g., severe preeclampsia). The invention features methods for measuring for the presence and level of serpina-1 and albumin polypeptides in a urine sample and utilizing the presence and/or level of such polypeptides to distinguish pregnant women with preeclampsia from pregnant women without preeclampsia, and to further distinguish women with milder preeclampsia from women with more severe preeclampsia or from controls without preeclamsia. Methods of the invention may also be used to assess the risk of a pregnant woman developing a specific complication of hypertensive disorders, including preeclampsia. Such complications may include delivery by caesarean section, increased serum uric acid, increased systolic and diastolic blood pressures, dipstick proteinuria, gravidity, fetal weight at delivery, placental abruption, IUGR, hemolysis, thrombocytopenia, elevated liver enzymes and HELLP syndrome (hemolysis, elevated liver enzymes, low platelet count).

In certain embodiments, a formula is used to analyze results of determination of the presence and/or amount of serpina-1 and albumin polypeptides in a sample from a subject. The resulting values provide information with respect to the likelihood that the pregnant woman has and/or will develop preeclampsia and/or may also be used to determine the severity of preeclampsia in a subject. As used herein, the term "formula" refers to any mathematical expression, algorithm or other metric that is useful in evaluating whether the levels of a biomarker(s) of interest indicate that a pregnant subject has or is at risk of developing preeclampsia and/or developing one or more complications of hypertensive disorders.

In some embodiments of the invention, SELDI-based methods of identifying subjects with preeclampsia may be used. Such methods may include a step for detecting the level of up to 13 serpina-1 and albumin polypeptide biomarkers. The method is based, in part, on a correlation between the presence of serpina-1 and albumin polypeptide biomarkers and the presence of preeclampsia. Thirteen serpina-1 and albumin polypeptide biomarkers have been identified, a subset are set forth herein as SEQ ID NOs:1-6. It has been found that the presence in a sample from a subject of a number of the 13 biomarkers that is above certain cut-off values indicates the presence of preeclampsia in the subject. In such embodiments of the invention, two objective urinary proteomic scores (UPS) are calculated: a Boolean score (UPSb), which represents the sum of Boolean indicators assigned to each of the 13 biomarkers complemented by a ranked score (UPSr), which retains the quantitative information of the 13 biomarkers with Boolean indicators of 1 (i.e., objectively present) and is calculated as a rounded integer with the following formula: UPSr=[S/N/10]+1, with S/N=signal to noise from SELDI analysis. Thus, in theory, the UPSb ranges from 0 to a maximum of 13 (one for each of the serpina-1 and albumin polypeptide biomarkers) and the UPSr can range from 0 to infinity. Optimum cut-off values as used for both UPSb and UPSr to discriminate between subjects with severe preeclampsia and controls without severe preeclampsia. A UPSb level greater than six and a UPSr level greater than 8 indicate that the subject has severe preeclampsia. A UPSb level less than 6 and a UPSr level less than 8 indicate that the subject does not have severe preeclampsia. If a sample is determined to have any other combination of values for UPSb and UPSr, a subsequent sample may be obtained from the subject at a time of 1, 2, 3, 4, 5, 6, or more days after the first sample was obtained and the second sample may be tested using methods of the invention to determine the status of the subject with respect to preeclampsia.

It will be understood that the above-described embodiment is an example of a manner in which the presence and/or level of serpina-1 polypeptides and/or albumin polypeptides may be assessed as a measure of preeclampsia status in a subject. In some embodiments of the invention, detection of predetermined combinations of biomarkers may be useful to assess the presence and or severity of preeclampsia in a subject. In certain embodiments of the invention, alternative correlations of serpina-1 polypeptides and albumin polypeptides with preeclampsia may be used to determine alternative cut-off values and measurements for diagnosing preeclampsia and/or for determining the severity of preeclampsia in a subject. In some embodiments serpina-1 polypeptide and/or albumin polypeptide may be quantitatively assessed in methods of diagnosing preeclampsia and/or the severity of preeclampsia in a subject.

1. Test Sample Preparation

In certain aspects, a sample from a subject may be a sample collected from a pregnant subject, e.g., a pregnant subject in whom preeclampsia status is to be assessed. A pregnant subject may be a pregnant woman who has been determined to have a high risk of preeclampsia based on her personal or family history. A pregnant subject may be a subject who has previously been diagnosed with chronic hypertension. Other subjects may include pregnant subjects who are known to have preeclampsia. In some embodiments, the methods of the invention may be used to monitor a subject diagnosed with preeclampsia, for example to determine the effectiveness of a therapy or treatment administered to the preeclamptic subject. Also, a subjects may be a healthy pregnant woman who is being tested for preeclampsia as part of a routine examination, or to establish a baseline level (e.g., a control or reference level) of the biomarkers in the subject or for other subjects. In other aspects, a sample may be collected from a pregnant non-human mammal, or a non-pregnant subject, for example, for use in methods to identify a compound to treat preeclampsia.

Biomarkers of the invention can be measured in different types of biological samples, preferably biological fluid samples such as urine. Biomarkers of the invention may also be assessed in tissues and/or in other biological fluid samples. Examples of other biological fluid samples that may be used in methods and kits of the invention, although not intended to be limiting, include blood, blood serum, plasma, vaginal secretions, CSF, tears, and saliva. If desired, a sample can be prepared to enhance detectability of the biomarkers. For example, a urine sample from the subject can be fractionated. Any method that enriches for a biomarker polypeptide of interest can be used. Sample preparations, such as prefractionation protocols, are optional and may not be necessary to enhance detectability of biomarkers depending on the methods of detection used. For example, sample preparation may be unnecessary if an antibody that specifically binds a biomarker is used to detect the presence of the biomarker in a sample.

Sample preparation may involve fractionation of a sample and collection of fractions determined to contain the biomarkers. Methods of prefractionation include, for example, size exclusion chromatography, ion exchange chromatography, heparin chromatography, affinity chromatography, sequential extraction, gel electrophoresis and liquid chromatography. Examples of methods of fractionation are described in PCT/US03/00531 (incorporated herein in its entirety).

As an example, a sample is pre-fractionated by anion exchange chromatography. Anion exchange chromatography allows pre-fractionation of the proteins in a sample roughly according to their charge characteristics. For example, a Q anion-exchange resin can be used, and a sample can be sequentially eluted with eluants having different pHs. Anion exchange chromatography allows separation of biomolecules in a sample that are more negatively charged from other types of biomolecules. Proteins that are eluted with an eluant having a high pH is likely to be weakly negatively charged, and a fraction that is eluted with an eluant having a low pH is likely to be strongly negatively charged. Thus, in addition to reducing complexity of a sample, anion exchange chromatography separates proteins according to their binding characteristics.

As another example, biomolecules in a sample can be separated by high-resolution electrophoresis, e.g., one or two-dimensional gel electrophoresis. A fraction containing a biomarker can be isolated and further analyzed by gas phase ion spectrometry. Preferably, two-dimensional gel electrophoresis is used to generate two-dimensional array of spots of biomolecules, including one or more biomarkers. See, e.g., Jungblut and Thiede, Mass Spectr. Rev. 16:145-162 (1997). The two-dimensional gel electrophoresis can be performed using methods known in the art. See, e.g., Deutscher ed., Methods In Enzyniology vol. 182. In certain cases, biomolecules in a sample are separated by, e.g., isoelectric focusing, during which biomolecules in a sample are separated in a pH gradient until they reach a spot where their net charge is zero (isoelectric point). This first separation step results in one-dimensional array of biomolecules. The biomolecules in one-dimensional array is further separated using a technique generally distinct from that used in the first separation step. Typically, two-dimensional gel electrophoresis can separate chemically different biomolecules in the molecular mass range from 1000-200,000 Da within complex mixtures. The pI range of these gels is about 3-10 (wide range gels).

As another example, high performance liquid chromatography (HPLC) can also be used to separate a mixture of biomolecules in a sample based on their different physical properties, such as polarity, charge and size. HPLC instruments typically consist of a reservoir of mobile phase, a pump, an injector, a separation column, and a detector. Biomolecules in a sample are separated by injecting an aliquot of the sample onto the column. Different biomolecules in the mixture pass through the column at different rates due to differences in their partitioning behavior between the mobile liquid phase and the stationary phase. A fraction that corresponds to the molecular weight and/or physical properties of one or more biomarkers can be collected. The fraction can then be analyzed by gas phase ion spectrometry to detect biomarkers. For example, the spots can be analyzed using either MALDI or SELDI as described herein.

Optionally, a biomarker can be modified before analysis to improve its resolution or to determine its identity. For example, the biomarkers may be subject to proteolytic digestion before analysis. Any suitable protease may be used. Proteases, such as trypsin, that are likely to cleave the biomarkers into a discrete number of fragments are particularly useful. The fragments that result from digestion may function as a fingerprint for the biomarkers, thereby enabling their detection indirectly. This is particularly useful where there are biomarkers with similar molecular masses that might be confused for the biomarker in question. Also, proteolytic fragmentation is useful for high molecular weight biomarkers because smaller biomarkers are more easily resolved by mass spectrometry. Optionally, the identity of the biomarkers can be further determined by matching the physical and chemical characteristics of the biomarkers in a protein database (e.g., SwissProt).

2. Detection and Measurement of Biomarkers

Biomarkers such as serpina-1 polypeptides and albumin polypeptides are preferably captured with capture reagents immobilized to a solid support, such as any biochip described herein, a multiwell microtiter plate, a resin, or other suitable support. A preferred mass spectrometric technique for use in the invention is Surface Enhanced Laser Desorption and Ionization (SELDI), as described, for example, in U.S. Pat. No. 5,719,060 and No. 6,225,047, in which the surface of a probe that presents the analyte to the energy source plays an active role in desorption/ionization of analyte molecules. In this context, the term "probe" refers to a device adapted to engage a probe interface and to present an analyte to ionizing energy for ionization and introduction into a gas phase ion spectrometer, such as a mass spectrometer. A probe typically includes a solid substrate, either flexible or rigid, that has a sample-presenting surface, on which an analyte is presented to the source of ionizing energy.

One version of SELDI, called "Surface-Enhanced Affinity Capture" or "SEAC," involves the use of probes comprised of a chemically selective surface ("SELDI probe"). A "chemically selective surface" is one to which is bound either the adsorbent, also called a "binding moiety,'" or "capture reagent," or a reactive moiety that is capable of binding a capture reagent, e.g., through a reaction forming a covalent or coordinate covalent bond.

The phrase "reactive moiety" here denotes a chemical moiety that is capable of binding a capture reagent. Epoxide and carbodiimidizole are useful reactive moieties to covalently bind polypeptide capture reagents such as antibodies or cellular receptors. Nitriloacetic acid and iminodiacetic acid are useful reactive moieties that function as chelating agents to bind metal ions that interact noncovalently with histidine containing peptides. A "reactive surface" is a surface to which a reactive moiety is bound. An "adsorbent" or "capture reagent" can be any material capable of binding a biomarker of the invention. Suitable adsorbents for use in SELDI, according to the invention, are described in U.S. Pat. No. 6,225,047.

One type of adsorbent is a "chromatographic adsorbent," which is a material typically used in chromatography. Chromatographic adsorbents include, for example, ion exchange materials, metal chelators, immobilized metal chelates, hydrophobic interaction adsorbents, hydrophilic interaction adsorbents, dyes, mixed mode adsorbents (e.g., hydrophobic attraction/electrostatic repulsion adsorbents). "Biospecific adsorbent" is another category, for adsorbents that contain a biomolecule, e.g., a nucleotide, a nucleic acid molecule, an amino acid, a polypeptide, a simple sugar, a polysaccharide, a fatty acid, a lipid, a steroid or a conjugate of these (e.g., a glycoprotein, a lipoprotein, a glycolipid). In certain instances, the biospecific adsorbent can be a macromolecular structure such as a multiprotein complex, a biological membrane or a virus. Illustrative biospecific adsorbents are antibodies, receptor proteins, and nucleic acids. A biospecific adsorbent typically has higher specificity for a target analyte than a chromatographic adsorbent.

Another version of SELDI is Surface-Enhanced Neat Desorption (SEND), which involves the use of probes comprising energy absorbing molecules that are chemically bound to the probe surface ("SEND probe"). The phrase "Energy absorbing molecules" (EAM) denotes molecules that are capable of absorbing energy from a laser desorption ionization source and, thereafter, contributing to desorption and ionization of analyte molecules in contact therewith. The EAM category includes molecules used in MALDI, frequently referred to as and is exemplified by cinnamic acid derivatives, sinapinic acid (SPA), cyano-hydroxy-cinnamic acid (CHCA) and dihydroxybenzoic acid, ferulic acid, and hydroxyaceto-phenone derivatives. The category also includes EAMs used in SELDI, as enumerated, for example, by U.S. Pat. No. 5,719,060.

Another version of SELDI, called Surface-Enhanced Photolabile Attachment and Release (SEPAR), involves the use of probes having moieties attached to the surface that can covalently bind an analyte, and then release the analyte through breaking a photolabile bond in the moiety after exposure to light, e.g., to laser light. For instance, see U.S. Pat. No. 5,719,060. SEPAR and other forms of SELDI are readily adapted to detecting a biomarker or biomarker profile, pursuant to the present invention.

The detection of the biomarkers according to the invention can be enhanced by using certain selectivity conditions, e.g., adsorbents or washing solutions. The phrase "wash solution" refers to an agent, typically a solution, which is used to affect or modify adsorption of an analyte to an adsorbent surface and/or to remove unbound materials from the surface. The elution characteristics of a wash solution can depend, for example, on pH, ionic strength, hydrophobicity, degree of chaotropism, detergent strength, and temperature.

In some embodiments of the invention, a sample is analyzed by means of a "biochip," a term that denotes a solid substrate having a generally planar surface, to which a capture reagent (adsorbent) is attached. Frequently, the surface of a biochip comprises a plurality of addressable locations, each of which has the capture reagent bound there. A biochip can be adapted to engage a probe interface and, hence, function as a probe, which can be inserted into a gas phase ion spectrometer, preferably a mass spectrometer. Alternatively, a biochip of the invention can be mounted onto another substrate to form a probe that can be inserted into the spectrometer.

A variety of biochips is available for the capture of biomarkers, in accordance with the present invention, from commercial sources such as Ciphergen Biosystems (Fremont, Calif.), Packard BioScience Company (Meriden, Conn.), Zyomyx (Hayward, Calif.), and Phylos (Lexington, Mass.). Exemplary of these biochips are those described in U.S. Pat. Nos. 6,225,047, 6,329,209, and in PCT Publication Nos. WO 99/51773 and WO 00/56934.

More specifically, biochips produced by Ciphergen Biosystems have surfaces presented on an aluminum substrate in strip form, to which are attached, at addressable locations, chromatographic or biospecific adsorbents. The surface of the strip is coated with silicon dioxide.

Illustrative of Ciphergen ProteinChip® arrays are biochips H4, SAX-2, WCX-2, and IMAC-3, which include a functionalized, crosslinked polymer in the form of a hydrogel, physically attached. to the surface of the biochip or covalently attached through a silane to the surface of the biochip. The H4 biochip has isopropyl functionalities for hydrophobic binding. The SAX-2 biochip has quaternary ammonium functionalities for anion exchange. The WCX-2 biochip has carboxylate functionalities for cation exchange. The IMAC-3 biochip has nitriloacetic acid functionalities that adsorb transition metal ions, such as $Cu^{++}$ and $Ni^{++}$, by chelation. These immobilized metal ions, in turn, allow for adsorption of biomarkers by coordinate bonding.

A substrate with an adsorbent is contacted with the urine sample for a period of time sufficient to allow biomarker that may be present to bind to the adsorbent. After the incubation period, the substrate is washed to remove unbound material. Any suitable washing solutions can be used; preferably, aqueous solutions are employed. An energy absorbing molecule then is applied to the substrate with the bound biomarkers. As noted, an energy absorbing molecule is a molecule that absorbs energy from an energy source in a gas phase ion spectrometer, thereby assisting in desorption of biomarkers from the substrate. Exemplary energy absorbing molecules include, as noted above, cinnamic acid derivatives, sinapinic acid and dihydroxybenzoic acid. Preferably sinapinic acid is used.

Once captured on a substrate, e.g., biochip or antibody, any suitable method can be used to measure one or more biomarkers in a sample. For example, biomarkers can be detected and/or measured by a variety of detection methods including for example, gas phase ion spectrometry methods, optical methods, electrochemical methods, atomic force microscopy and radio frequency methods. Using these methods, one or more biomarkers can be detected.

In one embodiment, methods of detection and/or measurement of the biomarkers use mass spectrometry and, in particular, SELDI. SELDI refers to a method of desorption/ionization gas phase ion spectrometry (e.g., mass spectrometry) in which the analyte is captured on the surface of a SELDI probe that engages the probe interface. In "SELDI MS," the gas phase ion spectrometer is a mass spectrometer. SELDI technology is described in more detail above.

In another embodiment, an immunoassay can be used to detect and analyze biomarkers in a sample. An immunoassay is an assay that uses an antibody to specifically bind an antigen (e.g., a biomarker). An immunoassay is characterized by the use of specific binding properties of a particular antibody to isolate, target, and/or quantify the antigen. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to a biomarker from specific species such as rat, mouse, or human can be selected to obtain only those polyclonal antibodies that are specifically reactive with that biomarker and not with other proteins, except for polymorphic variants and alleles of the biomarker. This selection may be achieved by subtracting out antibodies that cross-react with the biomarker molecules from other species.

Using purified biomarkers or their nucleic acid sequences, antibodies that specifically bind to a biomarker (e.g., serpina-1 polypeptide or albumin polypeptide) can be prepared using any suitable methods known in the art. See, e.g., Coligan, Current Protocols in Immunology (1991); Harlow & Lane, Antibodies: A Laboratory Manual (1988); Goding, Monoclonal antibodies: Principles and Practice (2d ed. 1986); Kohler & Milstein, Nature 256:495-497 (1975); Huse et al., Science 246:1275-1281 (1989); Ward et al., Nature 341:544-546 (1989).

Generally, a sample obtained from a subject can be contacted with the antibody that specifically binds the biomarker. Optionally, the antibody can be fixed to a solid support to facilitate washing and subsequent isolation of the complex, prior to contacting the antibody with a sample. Examples of solid supports include glass or plastic in the form of, e.g., a microtiter plate, a stick, a bead, or a microbead. Antibodies can also be attached to a probe substrate or a protein chip.

After incubating the sample with antibodies, the mixture is washed and the antibody-marker complex formed can be detected. This can be accomplished by incubating the washed mixture with a detection reagent. This detection reagent may be, e.g., a second antibody which is labeled with a detectable label. Exemplary detectable labels include magnetic beads, fluorescent dyes, radiolabels, enzymes (e.g., horse radish peroxide, alkaline phosphatase and others commonly used in an ELISA), and colorimetric labels such as colloidal gold or colored glass or plastic beads. Alternatively, the biomarker in the sample can be detected using an indirect assay, wherein, for example, a second, labeled antibody is used to detect bound biomarker-specific antibody, and/or in a competition or inhibition assay wherein, for example, a monoclonal antibody which binds to a distinct epitope of the biomarker is incubated simultaneously with the mixture.

Methods for measuring the amount or presence of an antibody-marker complex include, for example, detection of fluorescence, luminescence, chemiluminescence, absorbance, reflectance, transmittance, birefringence or refractive index (e.g., surface plasmon resonance, ellipsometry, a resonant mirror method, a gating coupler waveguide method or interferometry). Optical methods include microscopy (both confocal and non-confocal), imaging methods and non-imaging methods. Electrochemical methods include voltametry and amperometry methods. Radio frequency methods include multipolar resonance spectroscopy. Useful assays are well known in the art, including, for example, an enzyme immune assay (EIA) such as enzyme-linked immunosorbent assay (ELISA), a radioimmune assay (RIA), a Western blot assay, or a slot blot assay.

Immunoassays can be used to determine presence or absence of a biomarker in a sample as well as the quantity of a biomarker in a sample. The amount of an antibody-marker complex can be determined by comparing to a standard. A standard can be, e.g., a known compound or another protein known to be present in a sample. It is understood that the test amount of biomarker need not be measured in absolute units, as long as the unit of measurement can be compared to a control.

When the sample is measured and data is generated, e.g., by mass spectrometry, the data may then be analyzed by a computer software program. In certain cases, a biomarker bound to the substrate can be detected in a gas phase ion spectrometer. The biomarkers are ionized by an ionization source such as a laser, the generated ions are collected by an ion optic assembly, and then a mass analyzer disperses and analyzes the passing ions. The detector then translates information of the detected ions into mass-to-charge ratios. Detection of a biomarker typically will involve detection of signal intensity. Thus, both the quantity and mass of the biomarker can be determined.

Generally, data generated by desorption and detection of biomarkers can be analyzed with the use of a programmable digital computer. The computer program analyzes the data to indicate the number of biomarkers detected, and optionally the strength of the signal and the determined molecular mass for each biomarker detected. Data analysis can include steps of determining signal strength of a biomarker and removing data deviating from a predetermined statistical distribution. For example, the observed peaks can be normalized, by calculating the height of each peak relative to some reference. The reference can be background noise generated by the instrument and chemicals such as the energy absorbing molecule which is set as zero in the scale.

A computer can transform the resulting data into various formats for display. The standard spectrum can be displayed, but in one useful format only the peak height and mass information are retained from the spectrum view, yielding a cleaner image and enabling biomarkers with nearly identical molecular weights to be more easily seen, in another useful format, two or more spectra are compared, conveniently highlighting unique biomarkers and biomarkers that are up- or downregulated between samples. Using any of these formats, one can readily determine whether a particular biomarker is present in a sample.

Software used to analyze the data can include code that applies an algorithm to the analysis of the signal to determine whether the signal represents a peak in a signal that corresponds to a biomarker according to the present invention. Software also can subject the data regarding observed biomarker peaks to classification tree or artificial neural network (ANN) analysis, to determine whether a biomarker peak or combination of biomarker peaks is present that indicates a diagnosis of intra-amniotic inflammation.

3. Diagnosis Methods and Kits

In certain embodiments, the present invention relates to the proteomic analysis of urine to obtain information that correlates with the presence of preeclampsia in a subject. Proteomic analysis of urine, in accordance with the invention, provides a rapid, simple and reliable means of detecting in a patient who has or is at risk of developing preeclampsia.

In one embodiment, one or more of the biomarkers (e.g., serpina-1 polypeptides albumin polypeptides in urine) of the invention can be employed for determining the presence or absence of preeclampsia in a pregnant subject. A concentration of a biomarker may correlate with the severity of preeclampsia (e.g., mild or severe preeclampsia) and a determination of a quantity of a biomarker in a sample may b used to determine the severity of preeclampsia in a subject. It is known that neurologic manifestations, such as seizures or coma (eclampsia), stroke, hypertensive encephalopathy, headaches, and visual aberrations (scotomata, diplopia, amaurosis, homonymous hemianopsia, are common in severe preeclampsia (Douglas and Redman, Br Med J 1994, 309: 1395-1400).

In specific embodiments, the diagnostic/detection methods of the invention entails contacting a urine sample from a patient with a substrate, having an adsorbent thereon, under conditions that allow binding between the biomarker and the adsorbent, and then detecting the biomarker bound to the adsorbent by gas phase ion spectrometry, for example, mass spectrometry. As described above, other detection paradigms that can be employed to this end include optical methods, electrochemical methods (voltametry and amperometry techniques), atomic force microscopy, and radio frequency methods, e.g., multipolar resonance spectroscopy. Immunoassays in various formats, such as ELISA, likewise can be adapted for detection of biomarkers captured on a solid phase.

In certain embodiments, the present invention provides kits for aiding in the diagnosis of preeclampsia. The kits are used to detect or screen for the presence of biomarkers and combinations of biomarkers that are differentially present in samples from subjects with preeclampsia.

In one embodiment, the kit comprises a substrate having an adsorbent thereon, wherein the adsorbent is suitable for binding a biomarker of the invention, and a washing solution or instructions for making a washing solution, in which the combination of the adsorbent and the washing solution allows detection of the biomarker using gas phase ion spectrometry. In preferred embodiments, the kit comprises a immobilized metal affinity capture chip, such as the H4 chip.

In another embodiment, a kit of the invention may include a first substrate, comprising an adsorbent thereon, and a second substrate onto which the first substrate is positioned to form a probe, which can be inserted into a gas phase ion spectrometer. In another embodiment, an inventive kit may comprise a single substrate that can be inserted into the spectrometer.

In a further embodiment, such a kit can comprise instructions for suitable operational parameters in the form of a label or separate insert. For example, the instructions may inform a consumer how to collect the sample or how to wash the probe.

In some embodiments, a kit of the invention may include an agent that specifically binds to a biomarker of the invention. An example of such an agent may is an antibody or antigen-binding fragment thereof that may be used to detect a biomarker of the invention in a sample.

In some embodiments, a kit for use in a mass spec method of the invention may comprise two surfaces optimum for separation of the biomarkers (e.g., 13 biomarkers disclosed herein), premixed buffers, and an array with positive and negative control spots [where biological samples with known peak presence or absence and of standard intensities have been overlaid]. An array prepared with urine samples as described herein (e.g., see Example 5) are stable and can be read at a later time without specific storage conditions (other than darkness and dessication) and without loss in signal intensity.

Biomarkers according to the invention also are useful in the production of other diagnostic assays for detecting the presence of the biomarker in a sample. For example, such assays may comprise, as the "adsorbent," "binding moiety," or "capture reagent," an antibody to one or more of the biomarkers such as serpina-1 polypeptides and/or albumin polypeptides. An antibody may be mixed with a sample suspected of containing the biomarkers and monitored for biomarker-antibody binding. The biomarker antibody may labeled with a detectible label, such as a radioactive, colorimetric, or enzyme label. In a preferred embodiment, the biomarker antibody is immobilized on a solid matrix such that the biomarker antibody is accessible to biomarker in the sample. The sample then is brought into contact with the surface of the matrix, and the surface is monitored for biomarker-antibody binding.

4. Screening Methods

In certain embodiments, the present invention provides a method of identifying a compound to treat preeclampsia. For example, such methods may include: (a) administering a candidate compound to a subject; (b) comparing the level of serpina-1 polypeptides and/or albumin polypeptides in a test urine sample obtained from the subject with the level of serpina-1 polypeptides and/or albumin polypeptides in a control urine sample, wherein if the serpina-1 polypeptide and/or albumin polypeptide levels are lower in the test urine sample than in the control urine sample, the candidate compound is a compound that treats preeclampsia. Optionally the serpina-1 polypeptide and/or albumin polypeptide levels in urine are measured using an immunological assay (e.g., an ELISA), a protein chip assay, or surface-enhanced laser desorption/ionization (SELDI). This method includes measurement of modified forms of serpina-1 polypeptide and/or albumin polypeptide such as allelic variants of serpina-1 polypeptide and/or albumin polypeptide, etc. Preferably, the subject is a female human such as a pregnant woman.

There are numerous approaches to screening for therapeutic agents in preeclampsia therapy, which target one or more of the biomarkers (e.g., the serpina-1 polypeptide and/or albumin polypeptide levels). For example, high-throughput screening of compounds or molecules can be carried out to identify agents or drugs that treat preeclampsia. Test agents to be assessed can be any chemical (element, molecule, compound, drug), made synthetically, made by recombinant techniques or isolated from a natural source. For example, test agents can be peptides, polypeptides, peptoids, sugars, hormones, or nucleic acid molecules (such as antisense or RNAi nucleic acid molecules). In addition, test agents can be small molecules or molecules of greater complexity made by combinatorial chemistry, for example, and compiled into libraries. These libraries can comprise, for example, alcohols, alkyl halides, amines, amides, esters, aldehydes, ethers and other classes of organic compounds. Test agents can also be natural or genetically engineered products isolated from lysates or growth media of cells—bacterial, animal or plant—or can be the cell lysates or growth media themselves. Presentation of test compounds to the test system can be in either an isolated form or as mixtures of compounds, especially in initial screening steps. Compounds identified through the screening methods can then be tested in animal models of preeclampsia to assess their anti-preeclampsia activity in vivo.

While the detailed description presented refers to serpina-1 and albumin, it will be clear to one of ordinary skill in the art that the description can also apply to family members, homologs, naturally occurring allelic variants, isoforms, precursors and/or variants of each growth factor.

The practice of the present invention will employ, unless otherwise indicated, conventional techniques of cell biology, cell culture, molecular biology, microbiology, recombinant DNA, and immunology, which are within the skill of the art. Such techniques are described in the literature.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

EXAMPLES

Introduction

Biomarker discovery for predicting, diagnosing and monitoring severity and treatment effectiveness of preeclampsia (PE) useful to prevent preeclampsia and to reduce the incidence of fetal and maternal death. Experiments were performed to apply proteomics to define the best combination of urinary biomarkers that set PE apart from other proteinuric hypertensive conditions during pregnancy. By identifying these protein biomarkers information on mechanisms related to pathogenesis of PE has been obtained.

Example 1

Methods

Patients and Clinical Definitions:

Urine samples from 122 pregnant women admitted at Yale New Haven Hospital between March 2004 and September 2005 have been studied. Samples were collected under protocols approved by the Human Investigation Committee of Yale University. All participants provided informed consent prior to enrollment and all women solicited for enrollment agreed to participate. Subjects were recruited from women evaluated or admitted to or the Labor and Birth unit and the antepartum High and Low Risk units. Gestational age was established based on menstrual date and/or ultrasonographic examination prior to 20-weeks gestation. Women were clustered into clinical categories based on the clinical judgment of the practitioner at enrollment. In the clinical setting this judgment was based on the widely accepted clinical criteria for diagnosis and categorization of preeclampsia. (ACOG Committee on Practice Bulletins. Obstet Gynecol. 99(1):159-67, 2002.) Severe preeclampsia (sPE) was defined as systolic blood pressure of >160 mm Hg or diastolic >110 mm Hg on at least 2 occasions 6 hours apart, >5 grams in a 24-hour urinary protein excretion, and or persistent +3 proteinuria on dipstick testing. Other elements of the sPE definition included: in utero growth restriction (IUGR)<10-th percentile, persistent neurological symptoms (headache, visual disturbances), epigastric pain, oliguria (less than 500 mL/24 h), serum creatinine >1.0 mg/dL or any elements of HELLP syndrome: hemolysis, elevated liver enzymes (>2 times the normal), low platelet count (<100,000 cells/µL). Chronic hypertension (crHTN) was defined as a sustained elevation in BP>140/90 mm Hg before pregnancy or before 20 completed weeks gestation. (ACOG Committee on Practice Bulletins. Obstet Gynecol. 99(1):159-67, 2002.) Criteria for the diagnosis of superimposed preeclampsia (spPE) included the a diagnosis of crHTN (as defined herein) accompanied by new onset proteinuria (as defined for sPE) or a sudden increase in proteinuria (if present in early pregnancy), a sudden increase in blood pressure that met severe criteria and did not respond to medical therapy, or the presence of other severe preeclampsia criteria, with the exclusion of isolated fetal growth restriction. Mild preeclampsia (mPE) was defined as a diastolic blood pressure of at least 140/90 mmHg and urinary excretion of at least 0.3 grams proteins/24 hours urine specimens (or at least 1+ or greater on dipstick testing), each on two occasions 4-6 hours apart and no diagnosis of either sPE or spPE. FIG. 1 illustrates the stratification of the 122 cases based on clinical diagnosis of practitioners at the time of the urine sampling. However, given that such diagnoses generally belonged to several practitioners, at the time of enrollment one of the investigators also abstracted the clinical information in the medical record into a single semi-quantitative variable that was named the "objective clinical score of sPE features (OCS-sPE)". Briefly, Boolean indicators (1=present and 0=absent) were assigned for the clinical criteria listed in Table 1. OCS-sPE was calculated by summing these indicators for each case.

TABLE 1

Clinical contributors to the "objective clinical score of sPE features (OCS-sPE)"

| Contribution to OCS-sPE | Criterion |
|---|---|
| 1 point: | [SBP ≧ 140 or DBP ≧ 90] and proteinuria ≧ +1 |
| 1 point: | SBP ≧ 160 |
| 1 point: | DBP ≧ 100 |
| 1 point: | proteinuria ≧ +3 |
| 1 point: | neurological manifestations |
| 1 point: | AST(SGOT) and ALT(SGPT) > 35 U/L |
| 1 point: | IUGR |
| 1 point: | platelets < 100,000 cells/µL |

Collection of Biological Samples:

At enrollment a random urine sample (5-10 mL) was collected by standard use of sterile containers. All sPE women had a Foley catheter placed to allow for accurate monitoring of urinary output. Seventy percent of sPE women were enrolled before initiation of magnesium sulphate seizure prophylaxis. In the absence of a Foley catheter urine samples were collected using other techniques (bladder catheterization or "clean catch" method). A sample of blood was collected by venipuncture at the time of urine collection and allowed to clot. Serum and urine samples were spun at 3000×g at 4° C. for 20 min., the supernatant aliquoted and immediately stored at −800 C. All samples analyzed were collected prior to labor induction or Cesarean delivery.

Figure 2:
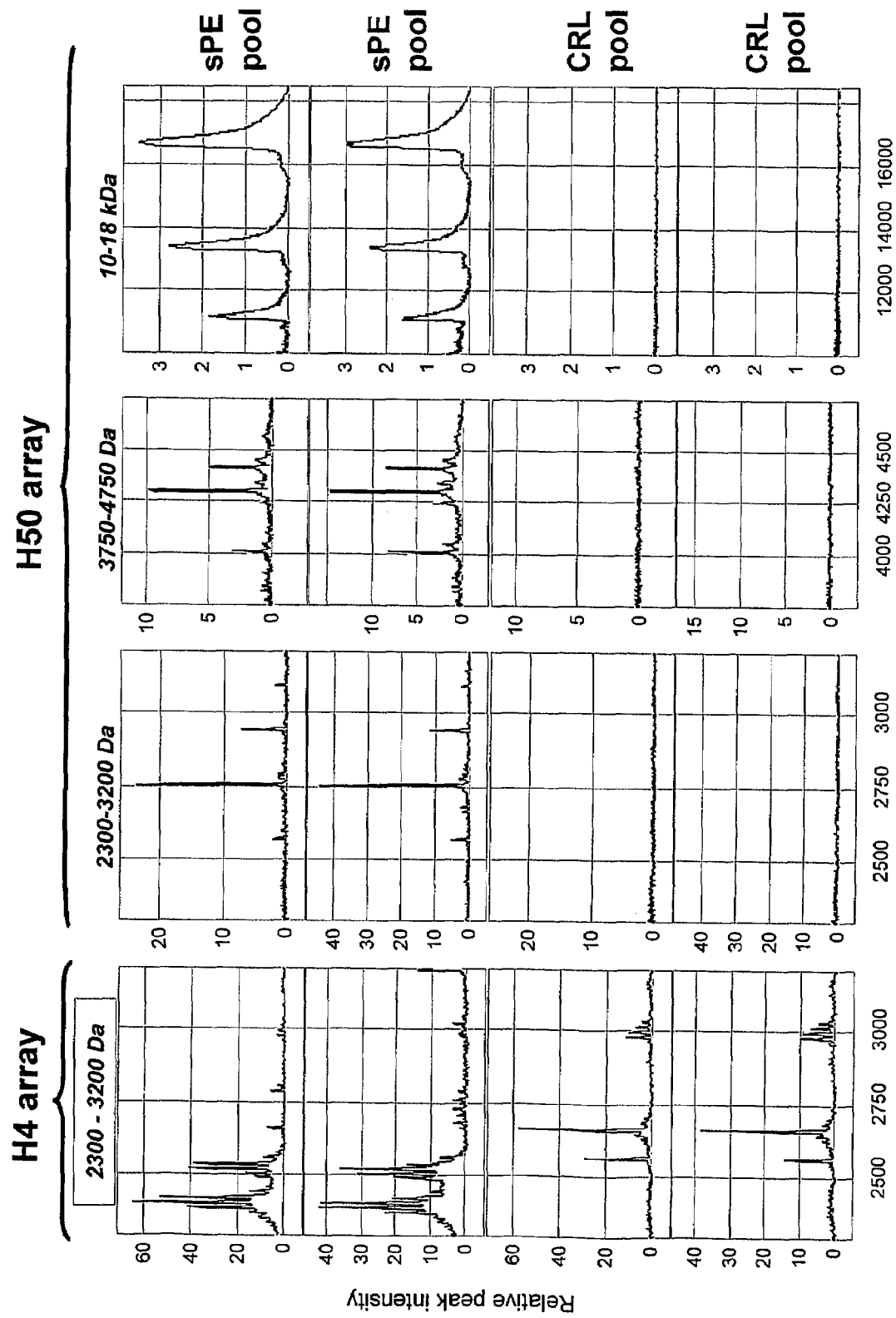
FIG. 2 shows of SELDI profiles obtained with the pooled urine samples from Phase 1 of the study. Abbreviations: sPE: severe preeclampsia; CRL: pregnant control.

A Study was Performed for Extraction of Meaningful Proteomic Profiles. The Study Evolved in Three Phases (FIG. 1):

Phase I: Optimization of conditions for protein profiling of urine using SELDI-TOF mass spectrometry. It was reasoned a priori that the wide fluctuation in total protein concentration in random urine samples would require dilutional normalization. Total protein concentration in urine samples was measured with a bicinchoninic acid/cupric sulfate reagent (BCA kit; Pierce, Rockford, Ill.). Two subgroups of cases were further delineated: from the CRL group 20 "selected CRL" were chosen to have no medical confounders, OCS-sPE values of zero at enrollment and a normal pregnancy course with term delivery (>37 completed wks of gestation) (FIG. 1). From the sPE group 20 "selected sPE" cases were chosen based on an OCS-sPE≧3 (i.e. at least 2 sPE features present) at enrollment and the practitioner's decision for a medically indicated delivery. Four "pools" were prepared (by pooling material from 10 of the selected pCRL or sPE, respectively) so that each sample contributes to each "pool" with an equal amount of protein as measured with the BCA kit. Various ProteinChip® array surfaces (Ciphergen Biosystems, Fremont, Calif.) were loaded with different amounts of protein (from 0.3 to 300 µg/mL) under various binding conditions as previously described. (Buhimschi, I. A. et al., BJOG 112: 173-181, 2005.; Norwitz, E. R. et al., Am J Obstet Gynecol 193: 957-64, 2005.) It was found that an on-spot application of 1.5 µg protein (diluted in 6 ul of binding buffer provided optimal signal-to-noise (S/N) ratios and was used in all subsequent experiments. The tested various array surfaces included reverse phase hydrophobic surfaces (H4: C-16 long chain aliphatic residues and H50: C6 to C12 aliphatic residues), strong anion exchanger carboxylate residues (Q10), weak cation exchanger quaternary ammonium (CM10) and metal affinity (IMAC30). For H4 chip surfaces optimization involved additional hydrophobic binding/washing gradients from 10 to 75% acetonitrile (for H4) combined with different trifluoroacetic acid concentrations (for H50 arrays). For Q10, CM10 and IMAC30 arrays binding was tested at various pHs (pH 4.0, 6.0, 7.4, 8.0, and 10.0). In addition, for IMAC30, affinity binding to the following metal anions $Zn^{2+}$, $Cu^{2+}$, $Ni^{2+}$, $Cd^{2+}$ and $Ga^{3+}$ was tested by overlaying the array surface with two applications of 100 mM $ZnSO_4$, $CuSO_4$, $NiSO_4$, $CdSO_4$ or $GaNO_3$. After 1-hour of incubation on the respective spots the sample was aspirated and the spots washed individually with 6 volumes of 20 µl of the respective binding buffer, left to air-dry for a few seconds and then overlaid with matrix solution diluted in 0.5% trifluoroacetic acid/50% acetonitrile. The matrix (energy absorbing molecule) consists of either 1-µl of a 20% saturated solution of a-cyano-4-hydroxycinnamic acid (CHCA), on one set of arrays or two sequential applications of 1 µl 50% saturated solution of sinnapinic acid (SPA). The chips were allowed again to air-dry for and then mass spectra recorded in the positive-ion mode in a Protein Biology System® IIC SELDI-TOF mass spectrometer (Ciphergen Biosystems), a linear laser desorption/ionization-time of flight mass spectrometer with time-lag focusing using the ProteinChip® software v 3.2.1. The instrument was externally calibrated using the [M+H]+ ion peaks of 1296.5 Da (angiotensin), 1570.6 Da ([Glu1]fibrinogen), 2147.5 Da (porcine dynorphin A [209-225]) and 5733.6 (bovine insulin). The resulting protein profile contained a fingerprint of the proteins bound optimally to the respective spots of the array separated by their mass/ charge ratio (m/z). Two experimental conditions (H4 and H50 arrays) appeared to differentiate between the pools from patients with sPE and those from CRLs by revealing several clusters of peaks common and unique to the sPE pools in several mass regions (FIG. 2).

Phase II: Definition of diagnostic profiles and proteomic scores. Next, all samples used to prepare the pools (n=40) were individually run in standardized conditions established in phase i. Briefly, the H4 array was prepared by preconditioning the spot surface with a 5 min. application of 6-µl 20% acetonitrile followed by application of urine samples also diluted with 20% acetonitrile (H4 binding buffer) each containing 0.25 mg/ml total protein. The H50 array was prepared by preconditioning the spots first with 50% acetonitrile for 5 min. and then by another 5 min. with a solution of 0.1% trifluoroacetic acid in 15% aqueous acetonitrile (H50 binding buffer). Finally, urine samples (6-µl) diluted to 0.25 mg/ml total protein using the same H50 binding buffer were applied to individual spots. On both types of arrays some spots were overlaid with the respective binding buffer alone and served to determine the level of "background noise". (Buhimschi, i.a. et al., BJOG 112: 173-181, 2005.) Following 1-hour incubation, unbound proteins were removed by washing each spot with the respective binding buffer. After air-drying, each spot was covered with two sequential layers of 1-p. 120% saturated CHCA solution and the arrays read in the seldi reader. This procedure (including protein measurement using the BCA kit) required approximately 2.5 hours.

Systematic manual analysis of SELDI tracings was based on the principles of "mass restricted [MR] scoring" (Buhimschi, I. A. et al., BJOG 112: 173-181, 2005; Buhimschi, C. S. et al., Obstet Gynecol Survey 61: 543-53, 2006.) with modifications (so that only criteria 1, 2, 3 and 5 were respected) and extracted a combination of 13 biomarker peaks (P1-P13) derived from the reading of both the H4 (P1-P4) and H50 (P5-P13) arrays in the low mass range (2.3-17.5 kDa). To further quantify the proteomic information based on these 13 biomarkers the mass (m/z+1) of each peak (as a reflection of biomarker identity) and its signal-to-noise ratio (S/N: as a measure of biomarker abundance) were exported to an Excel spreadsheet. A third parameter (presence or absence of each biomarker) was calculated from their S/N values. If the S/N ratio for each of the 13 peaks was greater than the a cut-off of average S/N+2 standard deviations for each corresponding mass from all spectra obtained from the spots covered with binding buffer alone then the biomarker peak was considered present and assigned a Boolean indicator of 1 as opposed to peaks below the cut-off which were assigned a Boolean indicator of 0.

Two objective urinary proteomic scores (UPS) were calculated: a Boolean score (UPSb) representing the sum of Boolean indicators assigned to each of the 13 biomarkers complemented by a ranked score (UPSr), which retains the quantitative information of the biomarkers with Boolean indicators of 1 (i.e., objectively present) and is calculated as a rounded integer with the following formula: UPSr=[S/N/10]+1. Thus, in theory UPSb ranges from 0 to a maximum of 13 while UPSr can range from 0 to infinity. Receiver operator characteristic (ROC) analysis was further used to establish optimum cut-offs for both UPSb and UPSr to discriminate between Phase II cases clinically classified as sPE from CRLs.

Phase III: Accuracy calculation. SELDI analysis was performed as described for Phase II for all 122 samples that were assigned randomly to new H4 and H50 arrays. UPSb and UPSr values were calculated for each tracing and their diagnostic performance compared with those of other used (dipstick test) or proposed (urine protein-to-creatinine ratio (Rodriguez-Thompson, D. & Lieberman, E. S. Am J Obstet Gynecol 185:808-11, 2001.), urinary Flt-1 and PlGF concentration and the ratio sFlt-1/PlGF (uFP). (Buhimschi, C. S. et al., Am J Obstet Gynecol 192: 734-41, 2005.)

Identification of the discriminatory proteomic biomarkers. To identify the discriminatory protein biomarkers new arrays were prepared from urine samples with highest UPSr scores. Tandem mass spectrometric peptide sequencing was accomplished using an quadrupole time of flight instrument (Q-TOF™ II, Micromass Ltd, UK) equipped with a PCI 1000 interface (Ciphergen Biosystems). (Merchant, M. & Weinberger, S. Electrophoresis 21; 1164-7, 2000.) Matrix conditions were identical to SELDI-TOF analysis described previously.

Other Biochemical and Immunochemical Estimates:

ELISA assays: ELISA assays for human unbound sFlt-1 and PlGF were performed according to the manufacturer's instructions (R&D Systems, Minneapolis, Minn.). Briefly, urine samples were assayed in duplicate in a 96-well plate precoated with a capture antibody directed against free sFlt-1 or PlGF. Incubation protocols were performed followed by washings and reading at 450 nm in accordance with the procedure summary. The minimal detectable concentrations in the assays for sFlt-1 and PlGF were 5 and 7 pg/mL, respectively. The data were reported and plotted using the Softmax software Pro 3.1.1 (Molecular Devices, Sunnyvale, Calif.). This software reports a positive value if the optical density of the sample wells is above that of the zero standard (Blank wells). If the optical density of a sample well is below that of the zero standard a negative value is reported and automatically converted to zero by the computer. The inter-assay and intra-assay coefficients of variation varied from 3 to 10%. Plates were read at 450 nm with 570 nm wavelength correction using a VERSAmax™ microplate reader with Softmax Pro 3.1.1 software.

For albumin immunoassays microtiter plates (Immuno MaxiSorp, Nalge Nunc, Rochester, N.Y.) were coated with capture antibody (10 µg/mL goat anti-human albumin antibody, Bethyl Laboratories). The plates were washed, blocked and incubated with urine (1:1000 dilution) or human albumin calibrants (Bethyl Laboratories) in a range from 6.25 to 400 ng/mL. Detection was accomplished using a goat anti-human albumin antibody conjugated to horseradish peroxidase (1:150,000 dilution, Bethyl Laboratories) and 3,3',5,5,'-tetramethylbenzidine (Vector Laboratories, Burlingame, Calif.) as substrate. The color reaction was stopped with 2M sulfuric acid and plates were read at 450 nm with 650 nm wavelength correction. The intra-assay coefficient of variation was less than 5%. The sensitivity of the assay was 1 ng/ml.

For alpha-1-antitrypsin (A1AT) immunoassays microtiter plates were coated with capture antibody (10 µg/mL sheep anti-human A1AT antibody, Affinity Biologicals, Ancaster, Canada). Urine samples were assayed at several dilutions (1:50-1:100,000) against a 7-point standard curve from 0.123 to 90 ng/mL. Detection was accomplished as for albumin ELISA with a sheep anti-human A1AT antibody horseradish peroxidase conjugated (1:5,000 dilution, Affinity Biologicals) as secondary antibody.

Creatinine levels in serum and urine were measured in the same aliquot used for immunoassays using a colorimetric assay (Stanbio Laboratory, Boerne, Tex.) against standard curves derived from known concentrations.

Statistical analysis: All data sets were subjected to normality testing using the Kolmogorov-Smirnov method and report the data as either mean and standard deviation (SD) (for normally distributed data) or as median with range (for non-normally distributed data). Pairwise Multiple Comparison Procedures were performed using One Way Analysis of Variance followed by Dunett's tests or Kruskal-Wallis ANOVA on Ranks followed by Dunn's tests as appropriate. Proportions were compared with Fisher's exact or Chi-square tests. Test accuracy (cases correctly classified/total number of cases), sensitivity, specificity, positive (PPV) and negative predictive values (NPV) were measured on receiver operator characteristic (ROC) plots using MedCalc (Broekstraat, Belgium) statistical software.

Results

Clinical characteristics of women: Table 2 illustrates the clinical characteristics of the cases as classified by practitioners at enrollment together with the value of OCS-sPE for each group.

TABLE 2

Maternal demographic and clinical characteristics of women at enrollment (n = 122)

|  | CRL (n = 36) | sPE (n = 38) | mPE (n = 16) | crHTN (n = 13) | spPE (n = 19) | p value |
|---|---|---|---|---|---|---|
| Age (y)[†] | 25 ± 6 | 26 ± 7 | 29 ± 6 | 34 ± 3*[#] | 29 ± 6 | p < 0.001 |
| Gravidity[‡] | 2 [1-6] | 1 [1-8] | 2 [1-8] | 4 [1-8][#] | 2 [1-7] | p = 0.002 |
| Parity[‡] | 0.5 [0-4] | 0 [0-6] | 0.5 [0-4] | 1 [0-5][#] | 1 [0-4] | p = 0.006 |
| Weight (kg)[‡] | 84 [51-108] | 85 [56-159] | 86 [68-142] | 111 [85-148]* | 81 [66-143] | p = 0.031 |
| GA (wks)[‡] | 27 [7-42] | 33 [24-41] | 36 [24-40]* | 34 [26-39] | 29 [17-39] | p = 0.004 |
| Systolic BP (mmHg)[‡] | 111 [90-133][#] | 150 [100-220]* | 150 [120-162]* | 168 [130-205]* | 166 [126-196]* | p < 0.001 |
| Diastolic BP (mmHg)[‡] | 63 [45-82][#] | 100 [90-130]* | 90 [70-106]* | 98 [70-120]* | 92 [62-132]* | p < 0.001 |
| Neurological symptoms (n [%])[¶] | 0 [0][#] | 17 [45]* | 6 [38]* | 2 [15] | 5 [26]* | p < 0.001 |
| OCS-sPE ≥ 2 (n [%]) | 0 [0][#] | 38 [100]* | 8 [50]*[#] | 7 [54]*[#] | 16 [84]*[#] | p < 0.001 |

[†]Data presented as mean ± SD and analyzed by One-Way ANOVA and Student-Newman-Keuls tests
[‡]Data presented as median [range] and analyzed by Kruskal-Wallis ANOVA and Dunn's tests
[¶]Data presented as proportions and analyzed by Chi square tests.
*p < 0.05 vs. CRL group:
[#]p < 0.05 vs. sPE group crHTN women group were significantly older and heavier compared to CRLs and of higher gravidity and parity compared to sPE patients. There was no difference in gestational age (GA) among groups at the time of sampling with exception of mPE who were more advanced in pregnancy compared to CRLs. All hypertensive groups had significantly higher blood pressure values compared to CRLs (mean arterial pressure: sPE: 123, mPE: 112; crHTN: 119, spPE: 115 vs. CRL: 81 mmHg, p<0.001) and a higher proportion of sPE, mPE and spPE women manifested neurological symptoms.

The clinical diagnosis was supported by clinical laboratory values that occurred in the hypertensive groups (Table 3).

TABLE 3

Clinical laboratory results of patients with preeclampsia work-up (n = 86)

|  | sPE (n = 38) | crHTN (n = 13) | mPE (n = 16) | spPE (n = 19) | p value |
|---|---|---|---|---|---|
| Dipstick proteinuria[†] | 3 [1-4] | 0 [0-3][#] | 1 [0-3][#] | 2 [0-4] | p < 0.001 |
| 24-h proteinuria (g/dL)[‡] | 3.3 [0.2-13.1] | 0.3 [0.1-0.5][#] | 1.3 [0.1-1.9] | 0.9 [0.1-5.3] | p < 0.001 |
| AST (U/L)[‡] | 32 [5-756] | 16 [8-36][#] | 20 [10-32][#] | 20 [12-175] | p = 0.001 |
| ALT (U/L)[‡] | 21 [8-550] | 12 [5-21][#] | 14 [5-28] | 16 [2-194] | p = 0.009 |
| Elevated liver enzymes (n [%])[¶] AST and ALT > 35 U/L | 14 [37] | 0 [0][#] | 0 [0][#] | 3 [16] | p < 0.001 |
| Platelets (cells/μL × $10^3$)[†] | 190 ± 87 | 254 ± 79 | 253 ± 86 | 245 ± 98 | p = 0.025 |
| Low platelets (n [%])[¶] Platelets < 100,000 cells/μL | 8 [21] | 0 [0] | 0 [0] | 2 [11] | p = 0.238 |
| LDH (U/L)[‡] | 261 [206-1300] | 216 [153-269] | 177 [133-269][#] | 221 [167-556] | p < 0.001 |
| Uric acid: (mg/dL)[†] | 6.7 ± 1.3 | 4.4 ± 1.3[#] | 5.2 ± 1.6[#] | 6.0 ± 1.1[#] | p < 0.001 |

[†]Data presented as mean ± SD and analyzed by One-Way ANOVA and Student-Newman-Keuls tests
[‡]Data presented as median [range] and analyzed by Kruskal-Wallis ANOVA and Dunn's tests
[¶]Data presented as proportions and analyzed by Chi square tests.
[#]p < 0.05 vs. sPE group
AST: aspartate aminotransferase;
ALT: alanine aminotransferase sPE women had greater degrees of proteinuria when screened with the rapid urinary dipstick test compared with crHTN and mPE but not spPE. However, by 24-h urinary protein excretion only women with crHTN had lower proteinuria compared to sPE. Patients with sPE had higher levels of uric acid compared to all other groups, while elevated liver enzyme values were more often present in sPE and spPE women. As shown from Table 1, based on ACOG criteria (ACOG Committee on Practice Bulletins. Obstet Gynecol. 99(1):159-67, 2002.) a diagnosis of "preeclampsia" would require an OCS-sPE of at least 1 while any added criterion (i.e. OCS-sPE$\geq$2) would theoretically have entailed a diagnosis of sPE or spPE from the part of the practitioner. Although this was indeed the case for patients in CRL and sPE categories, for some of the patients in the other groups this rule did not apply confirming that the diagnosis and categorization of preeclampsia by practitioners is ultimately clinical. This observation justified the decision to further select cases for Phases I and II of the study design (FIG. 1) for the purpose of extracting meaningful and consistent urinary protein profiles. Furthermore, another consideration was the progressing nature of the preeclampsia syndrome especially in terms of disease severity and that the clinical classification may change. When the outcomes of the cases (Table 4) were examined it was found that both sPE and spPE groups delivered at a significantly earlier gestational age compared to CRLs and that the proportion of medically indicated preterm deliveries. In particular those at less than 34 weeks were increased in these groups. However, women with mPE at enrollment also had an increased proportion of indicated preterm deliveries for preeclampsia related issues.

TABLE 4

Outcome of cases (n = 122)

|  | CRL (n = 36) | sPE (n = 38) | mPE (n = 16) | crHTN (n = 13) | spPE (n = 19) | p value |
|---|---|---|---|---|---|---|
| GA at delivery (wks) ‡ | 39 [26-42]# | 34 [28-41]* | 37 [25-40] | 37 [28-39] | 35 [23-40]* | p < 0.001 |
| Delivery < 34 wks (n [%]) ¶ | 4 [11]# | 21 [55]* | 5 [31] | 3 [23] | 9 [47]* | p = 0.002 |
| Medically indicated delivery for sPE (n [%]) ¶ | 0 [0]# | 38 [100]* | 10 [63]*# | 3 [23]*# | 18 [95]* | p < 0.001 |
| Medically indicated delivery for sPE < 34 wks (n [%]) ¶ | 0 [0]# | 21 [55]* | 3 [19]*# | 1 [8]# | 9 [47]* | p < 0.001 |
| Delivery by C/S (n [%]) ¶ | 10 [28]# | 26 [68]* | 12 [75]* | 8 [61] | 11 [58] | p = 0.025 |
| Birthweight (grams) † | 3280 [920-4335]# | 1883 [902-4300]* | 2715 [440-4020] | 2270 [870-4120]* | 1810 [485-3340]* | p < 0.001 |

Figure 3:
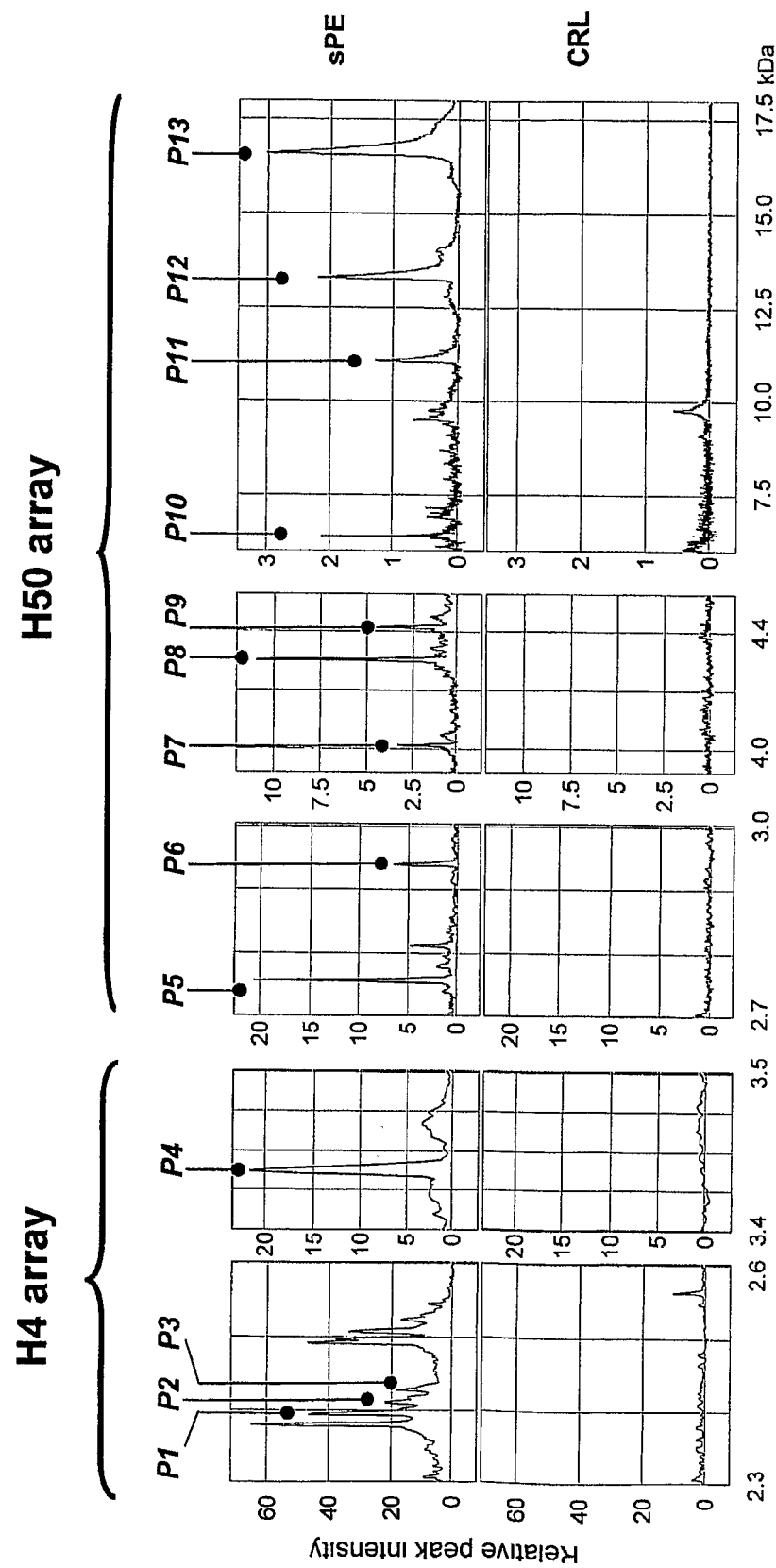
FIG. 3 shows representative SELDI profiles from one patient with severe preeclampsia (sPE) and control (CRL) illustrating the 13 diagnostic biomarkers components (P1-P13, marked with dots) of the urinary proteomic scores (UPSb and UPSr).

† Data presented as mean ± SD and analyzed by One-Way ANOVA and Student-Newman-Keuls tests
‡ Data presented as median [range] and analyzed by Kruskal-Wallis ANOVA and Dunn's tests
¶ Data presented as proportions and analyzed by Chi square tests.
*p < 0.05 vs. CRL group;
p < 0.05 vs. sPE group The urinary proteomic profile of preeclampsia. Component biomarkers, derived scores and cut-offs. At the end of Phase II of the study design a profile of 13 protein peaks (biomarkers P1-P13) was extracted as initially representative for the urine samples of the 19 "selected" sPE cases. FIG. 3 illustrates the SELDI profile obtained from urine of a representative patient in sPE group with an UPSb=13 (all biomarkers present) and a UPSr=47 as opposed to a CRL patient with both UPSb and UPSr=0 (all biomarkers absent). Table 5 lists the observed molecular mass of the 13 biomarkers and the frequency with which each biomarker was observed in urine samples of the patients enrolled in the study.

TABLE 5

Peak components of the urine proteomic score (UPS) of sPE

|  |  |  | Peak present n (%) | | |
|---|---|---|---|---|---|
|  |  | Observed SELDI mass | All samples | OCS-sPE ≥ 2 | |
| Peak |  | average [95% CI] Da | (n = 122) | No (n = 53) | Yes (n = 69) | p value |
| H4 array peaks | P1 | 2393.1 [2392.9-2393.3] | 22 (18%) | 1 (1%) | 21 (40%) | p < 0.001 |
|  | P2 | 2408.6 [2408.4-2408.9] | 28 (23%) | 5 (7%) | 23 (19%) | p < 0.001 |
|  | P3 | 2426.0 [2425.6-2426.4] | 20 (16%) | 2 (3%) | 18 (34%) | p < 0.001 |
|  | P4 | 3486.9 [3486.6-3487.2] | 23 (19%) | 2 (3%) | 21 (40%) | p < 0.001 |
| H50 array peaks | P5 | 2755.3 [2755.1-2755.4] | 91 (75%) | 38 (55%) | 53 (100%) | p < 0.001 |
|  | P6 | 2939.4 [2939.2-2939.5] | 59 (48%) | 11 (16%) | 48 (91%) | p < 0.001 |
|  | P7 | 4010.1 [4009.9-4010.4] | 49 (40%) | 6 (9%) | 43 (81%) | p < 0.001 |
|  | P8 | 4302.3 [4302.1-4302.4] | 71 (57%) | 18 (3%) | 52 (98%) | p < 0.001 |
|  | P9 | 4414.7 [4414.3-4415.1] | 68 (56%) | 20 (29%) | 48 (91%) | p < 0.001 |
|  | P10 | 6399.3 [6398.5-6400.1] | 87 (71%) | 35 (51%) | 52 (98%) | p < 0.001 |
|  | P11 | 11101.7 [11098.9-11104.4] | 69 (57%) | 17 (25%) | 52 (98%) | p < 0.001 |
|  | P12 | 13319.2 [13316.4-13321.9] | 79 (65%) | 26 (38%) | 53 (100%) | p < 0.001 |
|  | P13 | 16652.7 [16648.2-16657.2] | 80 (66%) | 27 (39%) | 53 (100%) | p < 0.001 |

Figure 4:
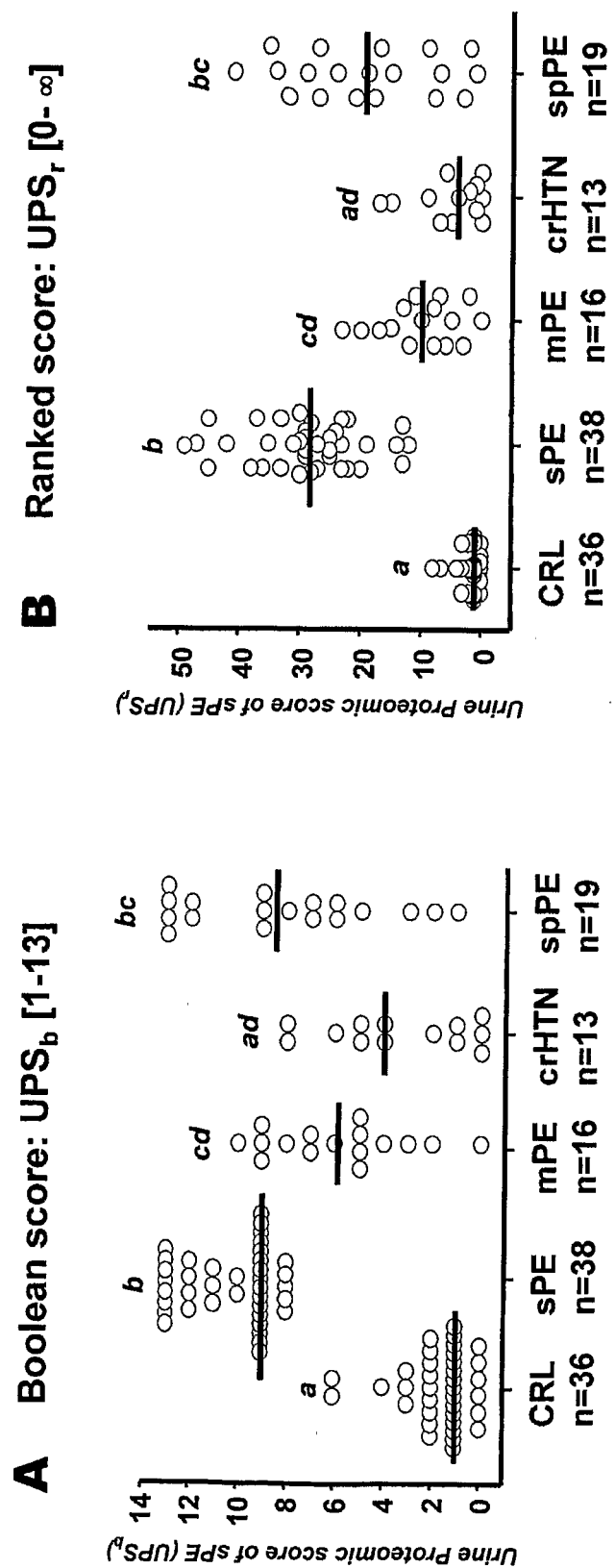
FIG. 4 shows UPSb (FIG. 4A) and UPSr (FIG. 4B) scores for the 122 patients grouped by the clinical classification of the practitioner at the time of urine collection. The horizontal black bar represents the median of each group. Values with at least one common superscript are statistically not different at a value of $p>0.05$ (Kruskall-Wallis ANOVA on Ranks, followed by multiple Dunn's tests).
Figure 7:
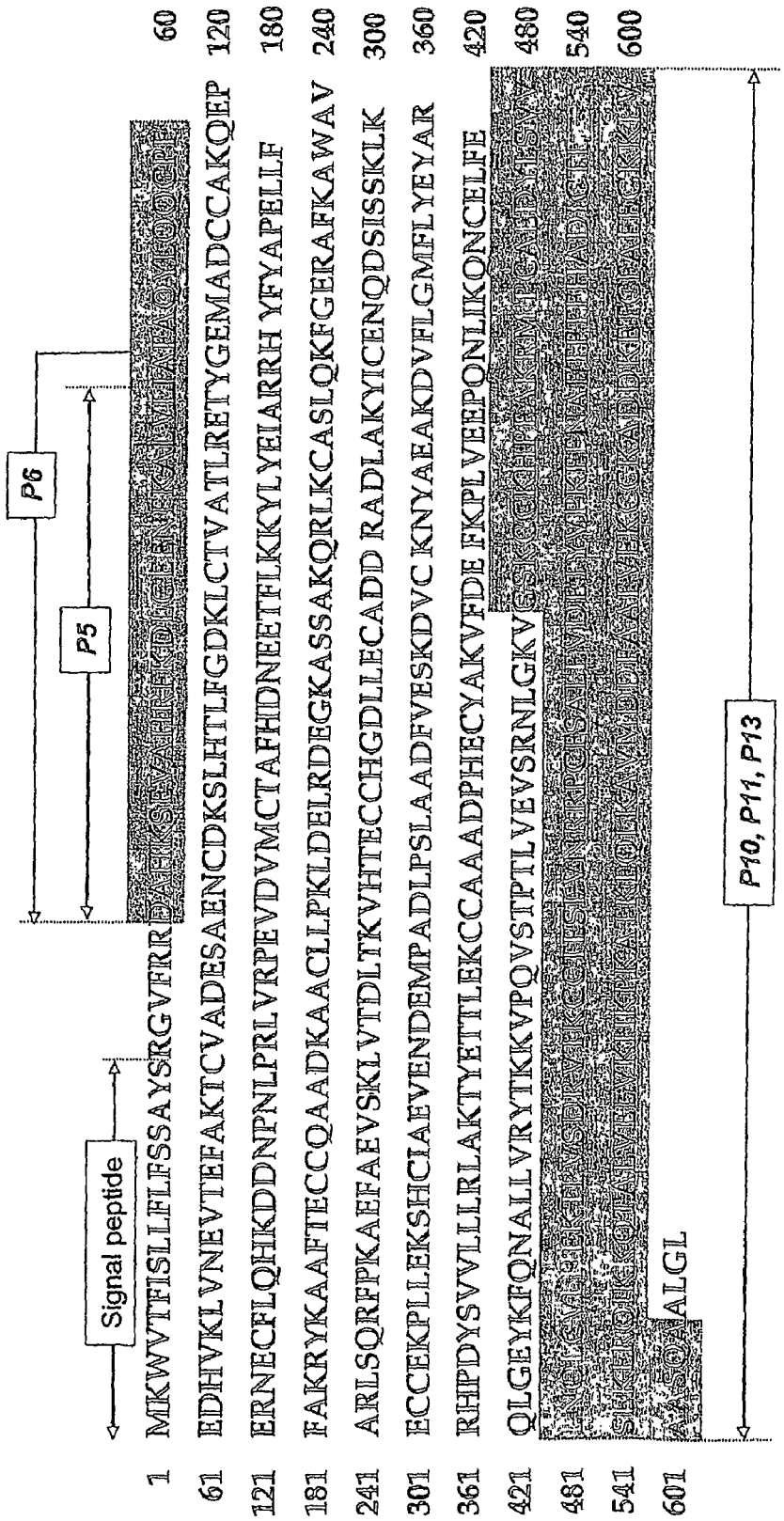
FIG. 7 provides the sequence of albumin (SEQ ID NO:8; Genbank Accession No. P02768). A shaded region indicates the sequences of P5, and P6 and a second shaded region (set forth herein as SEQ ID NO:10) provides the region of that includes P10, P11, and P13.

Each biomarker was present more often (p<0.001) in urine of patients that had an OCS-sPE≧2. FIG. 4 presents the distribution of the composite scores UPSb (FIG. 4A) and UPSr (FIG. 4B) for all patients in the study based on the clinical category at enrollment. sPE women had significantly elevated UPS scores compared to all groups except spPE. crHTN patients without spPE had scores no different than controls.

To determine the cut-off levels for the two proteomic scores that could be used further for disease classification ROC analysis was applied first to sPE and CRL groups due to the concurrence for these groups of a clinical diagnosis of sPE with an OCS-sPE≧2. It was established that the combination of an UPSb>6 and an UPSr>8 predicted with 100% sensitivity and 100% specificity a diagnosis of sPE at the time of urine collection (area under the ROC curve=1.00 [95% CI: 0.95-1.00]).

Proteomic analysis of urine is a simple and objective method to diagnose and classify hypertensive and proteinuric diseases of pregnancy. Presence of specific fragments of albumin and serpina-1 are highly characteristic for preeclampsia, whether or not the preeclampsia is superimposed on chronic hypertension. In addition, the identified proteins provided insight into a novel pathological mechanism of PE.

Example 2

Ability of Proteomic Profiling of Urine to Predict Development of Preeclampsia

A group of women at either low risk or at high risk of developing preeclampsia were followed longitudinally. Pre-pregnancy conditions for the high-risk group included: chronic hypertension, a history of severe preeclampsia, poorly controlled diabetes, diabetic nephropathy, nephrolitiasis and/or sickle cell disease with history of crisis. Since the initiation of this longitudinal arm of the study in March 2006 a group of 11 women have known outcomes (3 low risk and 8 high risk). 3 of the 11 women developed either preeclampsia or superimposed preeclampsia. FIG. 5 shows the urine proteomic scores acquired during pregnancy and before the clinically manifest disease. For the group that did not develop preeclampsia (white bars) and for the ones who did (black bars). The dashed line represents the cut-off of 6 in UPSb or 8 in UPSr. It has been established that for a women to be classified as preeclamptic based on urinary proteomic scores it is required that UPSb exceed 6 (7-13) and UPSr exceed 8. As seen in FIG. 5 the women who ultimately developed preeclampsia had elevated scores up to 15 weeks prior to the clinically manifest syndrome which required a medically indicated delivery).

Example 3

Quantification of Serum and Urine Serpina-1 Immunoreactivity in Preeclampsia

Background

Alpha-1 antitrypsin (A1AT or serpina-1) is an abundant plasma protein being the main blood-borne serine protease inhibitor. Although its primary function is the inhibition of neutrophil elastase [Luft F C. J Mol Med 1999; 77: 359-60] it also has activity against catepsin G, proteinase 3, pancreatic elastase, trypsin, chymotrypsin and collageanses [Lisowska-Myjak B. Clin Chim Acta. 2005; 352:1-13, kallikrein]. The antiproteolytic activity is explained by formation of 1:1 enzyme-A1AT complex. This results in the proteolytic cleavage of the reactive center peptide bond between Met 358 and Ser 359 of the secreted form of A1AT [Carrell R W. alpha 1-Antitrypsin: molecular pathology, leukocytes, and tissue damage. [J Clin Invest. 1986; 78:1427-31]. A1AT is synthesized by the liver, macrophages and neutrophils and also by trophoblast [Bergman D et al. Pediatr Res. 1993; 34: 312-7]. Increases in serum A1AT occur diseases such as rheumatoid arthritis, vasculitis, infections and other diseases associated with an inflammatory component [Ritchie R F et al. J Clin Lab Anal 2000; 14: 265-70]. Interestingly, studies have shown that even minor increases in levels of serum A1AT are associated with development of arterial hypertension and an increased risk of cardiovascular disease. [Arteriosler Thromb Vasc Biol 2002; 22: 2054-8; Engstrom et al. Stroke 2002; 33: 2744-9].

Methods

Paired serum-urine samples were collected from 22 severely preeclamptic (sPE) and 13 normal pregnant women (CRL). Additionally, placental biopsies were collected at delivery from women with sPE (n=5, GA: 31.6±3.0 wks) and gestational-age matched pregnancies with idiopathic preterm delivery without histological chorioamnionitis (n=5, GA=30.1±1.8 wks, p=0.68). Protein expression of A1AT was determined quantitatively by ELISA and qualitatively by western blotting and immunohistochemistry (IHC).

Results and Discussion

A1AT serum levels were significantly increased in sPE [14.9±0.7 µg/mg prot] compared to CRL [10.8±1.6 µg/mg prot; p=0.009], despite a significant increase in urinary excretion (>500 fold in sPE, p<0.001). In addition, urine and serum from women with sPE contained multiple immunoreactive forms of A1AT with molecular masses below (e.g., A1AT fragments) the 52 kDa mass of the A1AT. In the placenta, A1AT immunoreactivity localized largely intravascular and to villous macrophages and synctiotrophoblasts. The staining was significantly more evident in sPE compared with CTR. A1AT immunoreactivity is increased in preeclamptic serum, urine and placentas.

Pathophysiological Implications of the Diagnostic Biomarkers as Oxidized Fragments of Serpina-1. Evidence the Biomarkers Fragments of A1AT are Generated In Vivo.

From a pathophysiological perspective increased expression of a protein with antiproteolytic function may be detrimental to the process of placental invasion. This is in agreement with the thought that at the basis of preeclampsia lies the shallow invasion of the trophoblast. Characteristic for preeclampsia is the failure of the trophoblast to advance into the myometrial portion of the vessels which results in persistence of their muscular wall and potential for vasoconstriction and restriction of maternal blood flow to the placenta (Brosens I. J Obstet Gynaecol Br. Commonw 1964; 17: 222-30).

Another pathophysiological perspective is related to the susceptibility of A1AT to fragmentation in the context of oxidative stress. It is known that A1AT is oxidized by free radicals at its methionine residues resulting in loss of activity [Matheson N R et al Biochem Biophys Res Commun 1979; 88: 402-9]. Oxidized A1AT in blood has been evaluated in patients with rheumatoid arthritis using a monoclonal antibody which was found to recognize specifically oxidized A1AT [Ueda et al Clin Chim Acta 2002 317: 125-131. Preeclampsia is unanimously considered an oxidative stress disorder [an imbalance between pro-oxidant and antioxidant forces] (Walsh S W World Rev Nutr Diet 1994; 76 114-8.). Experiments have been performed to test whether in urine spiked and incubated with serpina-1 precursor one was unable to recreate any of the biomarkers that were identified as fragments of Serpina-1 by MS/MS analysis. The conclusion is that P1, P2, P3, and P7 originate only in vivo, possibly in the bloodstream in the context of severe preeclampsia, and are excreted by the kidney as fragments. Their oxidation may be an indication of the increase oxidative environment in preeclampsia and an antibody against oxidized A1AT may such pathological forms from the precursor.

It is significant that the fragment identified at the carboxy terminal as corresponding to P1-P2-P3 biomarkers is part of a sequence that has been shown to activate human monocytes to a pro-inflammatory state through interactions with the CD36 scavenger receptor and LDL receptor [Janciauskiene S et al Atherosclerosis. 2001; 158(1):41-51]. Preeclampsia has also been categorized as a pro-inflammatory condition with cytokines derived from the hypoxic placenta have been proposed to play a key role. Thus the circulating carboxy terminal fragment of A1AT may have also a pathogenic role in fueling inflammation and endothelial activation in preeclampsia.

Example 4

Using MS/MS corresponding sequences for five of the peaks (P1, P2, P3, P5 and P7) as shown in Table 6 were identified. The identified sequences matched to either the sequence of human serpina 1 (SwissProt P01009) or human albumin (SwissProt P02768). The corresponding masses of the peaks P1-P3 were resolved either by the SELDI-TOF MS instrument used to derive the urine profiles, by TOF-MS via the ProteinChip Tandem Interface. The fragmentation of P1 (2390.2 Da) was also determined using in MS/MS analysis.

measured by ELISA in the urine samples of the severe preeclampsia group (median concentration 0.22 mg/mL, n=38). Similarly the same urine samples were spiked with serpina-1 to a concentration of 0.1 mg/mL, equivalent to the concentration of immunoreactive serpina-1 measured by ELISA in the urine samples of our severe preeclampsia group that also had P1-P3 present (median concentration 0.11 mg/mL, n=15).

The appearance of P5 and P6 was observed in the urine sample spiked with albumin but not when albumin alone was applied on the H50 Protein chip array. The conclusion of the experiment is that it very likely P6 is also a fragment of albumin and is related with P5. An analysis of the N-terminal sequence of albumin that determined that the difference of 184 Da between P5 and P4 can be explained by the sum of masses of one isoleucine (aa position 49) and one alanine (aa position 50) residues flanking the carboxy terminal of the peptide sequence corresponding to P5. Thus it was predicted that the peptide sequence of P6 was: DAHKSEVAHRFKDL-GEENFKALVLIA (SEQ ID NO:6) [P02768 aa 25-50] with a computed mass of 2938.34 Da.

Moving toward higher masses the peaks were observed to appear in proximity to the masses of P8 and P10 in the urine sample spiked with albumin but not when albumin alone was applied on the H50 Protein chip array. Based on this the assumption was made that P8 and P10 are also fragments of albumin. Moreover, given that neither P6 nor P8 or P10 appeared when albumin alone was applied to the array it is likely their appearance in urine of patients with severe preeclampsia to be caused by the proteolytic cleavage of albumin

TABLE 6

Results obtained from the MS/MS analysis on selected peptides on the ProteinChip Tandem Interface

| Peak | Experimental mass SELDI-TOF MS | TOF-MS ES+ | Mowse score & expected value | Sequence | Calculated mass | Accession and residues |
|---|---|---|---|---|---|---|
| P1 | 2391.88 | 2390.27 | 72; 0.00097 | MIEQNTKSPLFMGKVVNPTQK | 2390.84 | P01009 aa 318-418 |
| P2 | 2407.81 | 2406.28 | 63; 0.0068 | $M_{ox}$IEQNTKSPLFMGKVVNPTQK | 2406.83 | P01009 aa 318-418 |
| P3 | 2429.72 | 2422.37 | 58; 0.039 | $M_{ox}$IEQNTKSPLFM$_{ox}$GKVVNPTQK | 2422.82 | P01009 aa 318-418 |
| P5 | 2755.18 | 2753.50 | 52; 0.086 | DAHKSEVAHRFKDLGEENFKALVL | 2754.10 | P02768 aa 25-48 |
| P7 | 4011.59 | 4010.28 | 34; 10 | EDPQGDAAQKTDTSHHDQDHPT FNKITPNLAEFAFS | 4011.20 | P01009 aa 25-60 |

Table 6: Sequence for P1, P2, P3, P5, and P7 are set forth as SEQ ID NO: 1, 2, 3, 5, and 4, respectively.

It was also determined by MS/MS analysis that the complex of peaks at 2504-2543 Da corresponds to the peptide LMIEQNTKSPLFMGKVVNPTQK (SEQ ID NO:9) [P01009 aa 317-418] in either no oxidation (observed TOF-MS mass 2390.27 Da) or with either one or two of the methionine residues (positions 398 and 409) in oxidized form.

Next it was investigated whether other peaks of the profile also corresponded to peptides derived from the interaction of these two proteins with the urinary milieu, but their identification was below the technical capabilities of the instrumentation. Thus an experiment was performed to artificially combine urine samples that lacked the biomarkers (control samples) with pure albumin or serpina-1 extracted from human serum. Thus, three urines from normal pregnant women were spiked with albumin to 0.25 mg/mL concentration. This value is equivalent to the concentration of albumin over poured in urine (i.e., in an interaction between the higher amount of albumin precursor and other components of urine).

An analysis of the mass range above 10 kDa revealed appearance of the pattern of peaks P11-P13 in the urine sample spiked with albumin but also when albumin alone was applied on the H50 Protein chip array. Based on this the assumption was made that P11-P13 are either the consequence of the fragmentation of albumin in the mass spectrometer or they were present as fragments also in the purified preparation used to spike the urine sample. However, regardless their origin it is very likely all three fragments originate from human albumin.

The analysis of the experiment where urine was spiked and incubated with serpina-1 was unable to recreate any of the biomarkers that were identified as fragments of Serpina-1 by MS/MS analysis. The conclusion is that P1, P2, P3, and P7 originate only in vivo, possibly in the bloodstream in the context of severe preeclampsia, and are excreted by the kidney as fragments. This conclusion led to the further investigation of the fragmentation of Serpina-1 using gel-electrophoresis and western blotting. These experiments further revealed that Serpina-1 was present in multiple immunoreactive forms in both urine and serum of women with severe preeclampsia. The masses of the forms indicate not only fragmentation but also polymerization.

Example 5

For SELDI analysis of urine, urinary protein was measured with BCA or other method and was adjusted with water to a working dilution of 2.5 mg/mL. For more diluted urine samples this step was omitted. The H4 array was prepared by preconditioning the spot surface with a 5 min. application of 6-µl 20% acetonitrile followed by application of urine samples diluted with 20% acetonitrile (H4 binding buffer) to 0.25 mg/mL total protein. The H50 array was prepared by preconditioning the spots first with 50% acetonitrile for 5 min. and then by another 5 min. with a solution of 0.1% trifluoroacetic acid in 15% aqueous acetonitrile (H50 binding buffer). Finally, urine samples (6-µl) diluted also to 0.25 mg/mL total protein using the same H50 binding buffer were applied to the individual spots. Following 1-hour incubation, unbound proteins were removed by washing each spot (6 times with a total volume of 120 µl of the respective binding buffer). After air-drying, each spot was covered with two sequential layers of 1-µL 20% saturated CHCA solution and the arrays read in the SELDI-TOF reader. This procedure (including protein measurement using the BCA kit) required approximately 2.5 hours.

If after assessment of the results from this assay, it was determined that the analysis should be repeated (e.g., there was no clear categorization of preeclampsia or no preeclampsia indicated by UPS scores) the patient is recommended to refrain from drinking fluids for a period of time [1-2 hours] to produce a more concentrated urine sample for analysis.

Urine samples analyzed by this mass spec method are stable. Thus, the biomarker peaks were found not to be susceptible to further proteolytic cleavage, which is in contrast to other analytes that have been analyzed with immunological methods (e.g., sFlt-1 and albumin precursor). Proteolytic cleavage was enhanced in sPE samples and sFlt-1 which is a larger molecule is more susceptible to degradation than PlGF which is smaller so one can get artificially lower values of the ratio in samples with significant degradation.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

EQUIVALENTS

Those skilled in the art will recognize, or be able to ascertain using no more than routine experimentation, many equivalents to the specific embodiments of the invention described herein. Such equivalents are intended to be encompassed by the following claims.

All references disclosed herein, including patent documents, are incorporated by reference in their entirety.

What is claimed is:

1. A method of determining that a pregnant woman has preeclampsia or is at increased risk of developing preeclampsia, comprising:
   (a) measuring a level of serpina-1 polypeptide and/or albumin polypeptide in a urine sample from the pregnant woman; and
   (b) comparing the level of serpina-1 polypeptide and/or albumin polypeptide in the urine sample with a reference value, wherein a higher level of serpina-1 polypeptide and/or albumin polypeptide in the urine sample relative to the reference value indicates that the pregnant woman has preeclampsia or is at increased risk of developing preeclampsia, wherein the albumin polypeptide comprises the amino acid sequence set forth as DAHKSEVAHRFKDLGEENFKALVL (SEQ ID NO:5) or DAHKSEVAHRFKDLGEENFKALVLIA (SEQ ID NO:6).

2. The method of claim 1, wherein the serpina-1 polypeptide and/or albumin polypeptide level is measured using an immunological assay.

3. The method of claim 1, wherein the serpina-1 polypeptide comprises the amino acid sequence set forth as MIEQNTKSPLFMGKVVNPTQK (SEQ ID NO:1), M$_{ox}$-IEQNTKSPLFMGKVVNPTQK (SEQ ID NO:2), M$_{ox}$-IEQNTKSPLFM$_{ox}$GKVVNPTQK (SEQ ID NO:3), or EDPQGDAAQKTDTSHHDQDHPTFNKITPNLAEFAFS (SEQ ID NO:4).

4. A method of determining that a pregnant woman has preeclampsia or is at increased risk of developing preeclampsia, comprising:
   (a) measuring a level of serpina-1 polypeptide and/or albumin polypeptide in a urine sample from the pregnant woman; and
   (b) comparing the level of serpina-1 polypeptide and/or albumin polypeptide in the urine sample with a reference value, wherein a higher level of serpina-1 polypeptide and/or albumin polypeptide in the urine sample relative to the reference value indicates that the pregnant woman has preeclampsia or is at increased risk of developing preeclampsia, wherein the albumin polypeptide is a fragment of the amino acid sequence set forth as GSKCCKHPEAKRMPCAEDYLSVVLNQLCVLHEKTPVSDRVTKCCTESLVNRRPCFSALEVDETYVPKEFNAETFTFHADICTLSEKERQIKKQTALVELVKHKPKATKEQLKAVMDDFAAFVEKCCKADDKETCFAEEGKKLVAASQAALGL (SEQ ID NO:10).

5. A method of identifying onset, progression, or regression of preeclampsia in a pregnant woman, comprising:
   (a) measuring a level of serpina-1 polypeptide and/or albumin polypeptide in a first urine sample obtained from the pregnant woman; and
   (b) measuring a level of serpina-1 polypeptide and/or albumin polypeptide in a second urine sample obtained from the same pregnant woman, wherein the second urine sample is obtained at a time subsequent to the time the first urine sample is obtained, wherein an increase in the serpina-1 polypeptide and/or albumin polypeptide level in the second urine sample relative to the serpina-1 polypeptide and/or albumin polypeptide level in the first urine sample identifies onset or progression of preeclampsia in the pregnant woman and a decrease in the serpina-1 polypeptide and/or albumin polypeptide level in the second urine sample relative to the serpina-1 polypeptide and/or albumin polypeptide level in the first urine sample identifies regression of preeclampsia in the pregnant woman, wherein the albumin polypeptide comprises the amino acid sequence set forth as DAHKSEVAHRFKDLGEENFKALVL (SEQ ID NO:5) or DAHKSEVAHRFKDLGEENFKALVLIA (SEQ ID NO:6).

6. The method of claim 5, wherein the serpina-1 polypeptide and/or albumin polypeptide is measured using an immunological assay.

7. The method of claim 5, wherein the serpina-1 polypeptide comprises the amino acid sequence set forth as MIEQNTKSPLFMGKVVNPTQK (SEQ ID NO:1), M$_{ox}$-IEQNTKSPLFMGKVVNPTQK (SEQ ID NO:2), M$_{ox}$-IEQNTKSPLFM$_{ox}$GKVVNPTQK (SEQ ID NO:3), or EDPQGDAAQKTDTSHHDQDHPTFNKITPNLAEFAFS (SEQ ID NO:4).

8. A method of determining that a pregnant woman has preeclampsia or is at increased risk of developing preeclampsia, comprising:
   (a) measuring a level of serpina-1 polypeptide and/or albumin polypeptide in a urine sample from the pregnant woman; and
   (b) comparing the level of serpina-1 polypeptide and/or albumin polypeptide in the urine sample with a reference value, wherein a higher level of albumin polypeptide in the urine sample relative to the reference value indicates that the pregnant woman has preeclampsia or is at increased risk of developing preeclampsia, wherein the albumin polypeptide is a fragment of the amino acid sequence set forth as GSKCCKHPEAKRMPCAEDYLSVVLNQLCVLHEKTPVSDRVTKCCTESLVNRRPCFSALEVDETYVPKEFNAETFTFHADICTLSEKERQIKKQTALVELVKHKPKATKEQLKAVMDDFAAFVEKCCKADDKETCFAEEGKKLVAASQAALGL (SEQ ID NO:10).

9. A method of assessing efficacy of a treatment for preeclampsia in a pregnant woman, comprising:
   (a) measuring the level of serpina-1 polypeptide and/or albumin polypeptide in a first urine sample obtained from the pregnant woman before the treatment for preeclampsia;
   (b) measuring the level of serpina-1 polypeptide and/or albumin polypeptide in a second urine sample from the same pregnant woman after the treatment for preeclampsia; and
   (c) comparing the level determined in (a) with the level determined in (b), wherein a decrease in the serpina-1 polypeptide and/or albumin polypeptide level in the second urine sample relative to the serpina-1 polypeptide and/or albumin polypeptide level in the first urine sample indicates the treatment for preeclampsia is effective and wherein no reduction in the serpina-1 polypeptide and/or albumin polypeptide level in the second urine sample relative to the serpina-1 polypeptide and/or albumin polypeptide level in the first urine sample indicates the treatment for preeclampsia is not effective, wherein the albumin polypeptide comprises the amino acid sequence set forth as DAHKSEVAHRFKDLGEENFKALVL (SEQ ID NO:5) or DAHKSEVAHRFKDLGEENFKALVLIA (SEQ ID NO:6).

10. The method of claim 9, wherein the serpina-1 polypeptide and/or albumin polypeptide is measured using an immunological assay.

11. The method of claim 9, wherein the serpina-1 polypeptide comprises the amino acid sequence set forth as MIEQNTKSPLFMGKVVNPTQK (SEQ ID NO:1), $M_{ox}$-IEQNTKSPLFMGKVVNPTQK (SEQ ID NO:2), $M_{ox}$-IEQNTKSPLFM$_{ox}$GKVVNPTQK (SEQ ID NO:3), or EDPQGDAAQKTDTSHHDQDHPTFNKITPNLAEFAFS (SEQ ID NO:4).

12. A method of determining that a pregnant woman has preeclampsia or is at increased risk of developing preeclampsia, comprising:
   (a) measuring a level of serpina-1 polypeptide and/or albumin polypeptide in a urine sample from the pregnant woman; and
   (b) comparing the level of serpina-1 polypeptide and/or albumin polypeptide in the urine sample with a reference value, wherein a higher level of albumin polypeptide in the urine sample relative to the reference value indicates that the pregnant woman has preeclampsia or is at increased risk of developing preeclampsia, wherein the albumin polypeptide is a fragment of the amino acid sequence set forth as GSKCCKHPEAKRMPCAEDYLSVVLNQLCVLHEKTPVSDRVTKCCTESLVNRRPCFSALEVDETYVPKEFNAETFTFHADICTLSEKERQIKKQTALVELVKHKPKATKEQLKAVMDDFAAFVEKCCKADDKETCFAEEGKKLVAASQAALGL (SEQ ID NO:10).

13. The method of claim 4, wherein the serpina-1 polypeptide and/or albumin polypeptide level is measured using an immunological assay.

14. The method of claim 8, wherein the serpina-1 polypeptide and/or albumin polypeptide level is measured using an immunological assay.

15. The method of claim 12, wherein the serpina-1 polypeptide and/or albumin polypeptide level is measured using an immunological assay.

* * * * *

UNITED STATES PATENT AND TRADEMARK OFFICE
CERTIFICATE OF CORRECTION

| | | |
|---|---|---|
| PATENT NO. | : 8,263,342 B2 | Page 1 of 1 |
| APPLICATION NO. | : 12/084004 | |
| DATED | : September 11, 2012 | |
| INVENTOR(S) | : Catalin S. Buhimschi et al. | |

It is certified that error appears in the above-identified patent and that said Letters Patent is hereby corrected as shown below:

IN THE SPECIFICATION

At column 1, line 17 immediately following the "RELATED APPLICATIONS" section, please insert the following paragraph:

-- GOVERNMENT SUPPORT

This invention was made with government support under HD047321 awarded by National Institutes of Health. The government has certain rights in the invention. --

Signed and Sealed this
Second Day of February, 2016

Michelle K. Lee
*Director of the United States Patent and Trademark Office*